(12) United States Patent
Wu

(10) Patent No.: US 9,175,027 B2
(45) Date of Patent: *Nov. 3, 2015

(54) POLYMER-CARBOHYDRATE-LIPID CONJUGATES

(76) Inventor: Nian Wu, North Brunswick, NJ (US)

(*) Notice: Subject to any disclaimer, the term of this patent is extended or adjusted under 35 U.S.C. 154(b) by 88 days.

This patent is subject to a terminal disclaimer.

(21) Appl. No.: 13/364,967

(22) Filed: Feb. 2, 2012

(65) Prior Publication Data

US 2012/0202979 A1   Aug. 9, 2012

Related U.S. Application Data

(60) Provisional application No. 61/440,488, filed on Feb. 8, 2011.

(51) Int. Cl.

| | | |
|---|---|---|
| *A61K 31/7032* | (2006.01) | |
| *A61K 31/231* | (2006.01) | |
| *A61K 31/25* | (2006.01) | |
| *A61K 31/325* | (2006.01) | |
| *A61K 31/4188* | (2006.01) | |
| *A61K 31/223* | (2006.01) | |
| *A61K 31/575* | (2006.01) | |
| *C07H 1/00* | (2006.01) | |
| *A61K 31/05* | (2006.01) | |
| *A61K 47/26* | (2006.01) | |
| *C07H 15/04* | (2006.01) | |
| *C08G 65/329* | (2006.01) | |
| *C07J 41/00* | (2006.01) | |
| *A61K 9/00* | (2006.01) | |
| *A61K 9/20* | (2006.01) | |

(52) U.S. Cl.
CPC ........ *C07H 1/00* (2013.01); *A61K 31/05* (2013.01); *A61K 31/223* (2013.01); *A61K 31/231* (2013.01); *A61K 31/25* (2013.01); *A61K 31/325* (2013.01); *A61K 31/4188* (2013.01); *A61K 31/575* (2013.01); *A61K 31/7032* (2013.01); *A61K 47/26* (2013.01); *C07H 15/04* (2013.01); *C07J 41/0061* (2013.01); *C08G 65/329* (2013.01); *A61K 9/0014* (2013.01); *A61K 9/0019* (2013.01); *A61K 9/0048* (2013.01); *A61K 9/0095* (2013.01); *A61K 9/2013* (2013.01); *C08L 2203/02* (2013.01)

(58) Field of Classification Search
None
See application file for complete search history.

(56) References Cited

U.S. PATENT DOCUMENTS

| | | | |
|---|---|---|---|
| 6,309,633 B1 * | 10/2001 | Ekwuribe et al. | ............ 424/85.1 |
| 2003/0215395 A1 | 11/2003 | Yu et al. | |
| 2010/0210518 A1 | 8/2010 | Keller et al. | |
| 2010/0260817 A1 * | 10/2010 | Slobodkin et al. | ............ 424/426 |

FOREIGN PATENT DOCUMENTS

| | | | | |
|---|---|---|---|---|
| RU | 2327702 C2 | 6/2008 | | |
| WO | WO0078302 | 12/2000 | | |
| WO | WO2006050072 | 5/2006 | | |
| WO | WO 2008100288 A2 * | 8/2008 | ............ | A61K 38/17 |
| WO | WO2010085347 | 7/2010 | | |
| WO | WO2010107487 | 9/2010 | | |
| WO | WO2010141069 | 12/2010 | | |
| WO | WO2011005980 | 1/2011 | | |

OTHER PUBLICATIONS

Zalipsky S et al: "Poly(Ethylene 1-15 Glycol)-Grafted Liposomes With Oligopeptide or Oligosaccharide Ligands Appended to the Termini of the Polymer Chains", Bioconjugate Chemistry, ACS, Washington, DC, US, vol. 8, No. 2, Mar. 1, 1997, pp. 111-118, XP000858875, ISSN: 1043-1802, DOI: 10.1021/BC9600832 figure 1.

Yiguang Wang et al., "Pegylated Phospholipids-Based Self-Assembly with Water Soluble Drugs", Pharmaceutical Research, 2010, vol. 27, No. 2, pp. 361-370, Abstract, Fig. 1, Chemical Structures C, A, B, p. 362, col. 1, paragraphs 1, 2, col. 2, last paragraph, p. 363, col. 2, last paragraph, p. 364, col. 1, first paragraph.

* cited by examiner

*Primary Examiner* — Layla Bland
*Assistant Examiner* — Bahar Craigo
(74) *Attorney, Agent, or Firm* — Steve Witters; Witters & Associates

(57) ABSTRACT

The invention comprises compounds, methods of making, and methods of using. The compounds may have a backbone and three appended functional groups: one lipid, one hydrophilic polymer, and one carbohydrate. Specific functional groups may be selected for specific applications in formulating pharmaceuticals, cosmetics, nutriceuticals, and the like. A variety of linkers between the backbone and functional groups may also be selected to optimize performance.

1 Claim, 5 Drawing Sheets

POLYMER-CARBOHYDRATE-LIPID CONJUGATES

This application claims priority to the provisional patent application Ser. No. 61/440,488, entitled "Polymer-Carbohydrate-Lipid Conjugates" filed in the U.S. Patent and Trademark Office on Feb. 8, 2011, by Nian Wu and to patent application Ser. No. 13/354,726, entitled "Polymer-Carbohydrate-Lipid Conjugates" filed in the U.S. Patent and Trademark Office on Jan. 20, 2012, by Nian Wu.

FIELD OF THE INVENTION

The present invention relates to polymer-carbohydrate-lipid conjugates, detailed and specific disclosures are given for synthetic polyethyleneglycol (PEG)-lipid conjugates preferably having substantially monodisperse PEG chains if used for intravenous drug administration. More particularly, the present invention relates to new polymer-carbohydrate-lipid conjugates and their use for drug delivery, cosmetics and other purposes.

BACKGROUND OF INVENTION

Polyethylenglycol (PEG) is widely used as a water soluble carrier for polymer-drug conjugates. PEG is undoubtedly the most studied and applied synthetic polymer in the biomedical field [Duncan, R. *Nature Rev. Drug Discov.* 2003, 2, 347-360]. As an uncharged, water-soluble, nontoxic, nonimmunogenic polymer, PEG is an ideal material for biomedical applications. Covalent attachment of PEG to biologically active compounds is often useful as a technique for alteration and control of biodistribution and pharmacokinetics, minimizing toxicity of these compounds [Duncan, R. and Kopecek, J., *Adv. Polym. Sci.* 57 (1984), 53-101]. PEG possesses several beneficial properties: very low toxicity [Pang, S. N. J., *J. Am. Coil. Toxicol,* 12 (1993), 429-456], excellent solubility in aqueous solutions [Powell, G. M., *Handbook of Water Soluble Gums and Resins*, R. L. Davidson (Ed.), Ch. 18 (1980), MGraw-Hill, New York], and extremely low immunogenicity and antigenicity [Dreborg, S, *Crit. Rev. Ther. Drug Carrier Syst.,* 6 (1990), 315-365]. The polymer is known to be non-biodegradable, yet it is readily excretable after administration into living organisms. In vitro study showed that its presence in aqueous solutions has shown no deleterious effect on protein conformation or activities of enzymes. PEG also exhibits excellent pharmacokinetic and biodistribution behavior. [Yamaoka, T., Tabata, Y. and Ikada, Y., *J. Pharm. Sci.* 83 (1994), 601-606].

Over last three decades, some of promising drug carriers that have been investigated in systemic delivery systems includes liposomes, polymeric nanoparticles, polymeric micelles, ceramic nanoparticles and dendrimers (Cheman et al. *Drug. Dev. Ind. Pharm,* 26: (2000) 459-463; Lian and Ho. *J. Pharm. Sci,* 90 (2001) 667-680; Adams et al. *Pharm. Sci,* 92 (2003) 1343-1355; Na et al. *Eur. J. Med. Chem,* 41 (2006) 670-674; Kaur et al. *J. Control, Rel,* 127 (2008) 97-109). Systemic drug delivery can be achieved by intravenous or intraperipheral injection and therefore is non-invasive. The drugs may be administered repeatedly as needed. However, in order to achieve therapeutic concentrations at the target site, systemic administration requires large dosages with relatively high vehicle contents which may cause side effects such as allergic reactions ["Cremophor-based paclitaxel 'chemo' drug triggers fatal allergic reactions," *The Medical News.* 9 Jun. 2009].

In the design of safe and biocompatible delivery systems, several important factors must be taken into account including high solubilization properties and retaining power of the carrier and appropriate surface characteristics to permit interactions with potential targeting tissue sites or cell membrane permeations.

The important role of sugars in many specific interactions in living systems is well recognized. Large molecular weight carriers such as proteins or liposomes can be modified with sugars for specific drug delivery (Monsigny M, Roche A C, Midoux P and Mayer R., *Adv Drug Delivery Rev.,* 14 (1994): 1-24; Palomino E. *Adv Drug Delivery Rev.,* 13 (1994)311-323]. Lipid-sugar particles have been used for drug delivery to the brain for providing prolonged duration local anesthesia when injected at the sciatic nerve in rats [Kohane D S, Lipp M, Kinney R., Lotan N, Langer R., *Pharm. Res.* 17 (2000) 1243-1249]. Since sugar-lipids are composed of materials that occur naturally in the human body suggests potential advantages over some other polymer-based controlled-release terms of biocompatibility [Kohane D S, Lipp M, Kinney R, Anthony D, Lotan N, Langer R., *J. Biomed. Mat. Res.* 59 (2002) 450-459; Menei P, Daniel V, Montero-Menei C, Brouillard M, Pouplard-Barthelaix A, Benoit J P., *Biomaterials,* 14 (1993) 470-478]. Lipid-sugars have a good biocompatibility as shown by the results of the in vitro and in vivo studies [Kohane D S, Lipp M, Kinney R, Anthony D, Lotan N, Langer R., *J. Biomed. Mat. Res.* 59 (2002) 450-459].

Narrow molecular weight distribution of drug delivery polymers is crucially important for biomedical applications, especially if used for intravenous injections. For instance, PEG-8 Caprylic/Capric Glycerides are mixtures of monoesters, diesters, and triesters of glycerol and monoesters and diesters of polyethylene glycols with a mean relative molecular weight between 200 and 400. Partially due to allergic reactions observed in animals, the application of PEG-8 CCG for many water-insoluble drugs was restricted and a dose limit of approximately 6% of PEG-8 CCG was used for human oral drug formulations.

BRIEF SUMMARY OF THE INVENTION

The invention comprises compounds having a backbone and three appended functional groups: one lipid, one hydrophilic polymer, and one carbohydrate. Specific functional groups may be selected for specific applications in formulating pharmaceuticals, cosmetics, nutriceuticals, and the like. A variety of linkers between the backbone and functional groups may also be selected to optimize performance.

ABBREVIATION LIST

Figure 1:
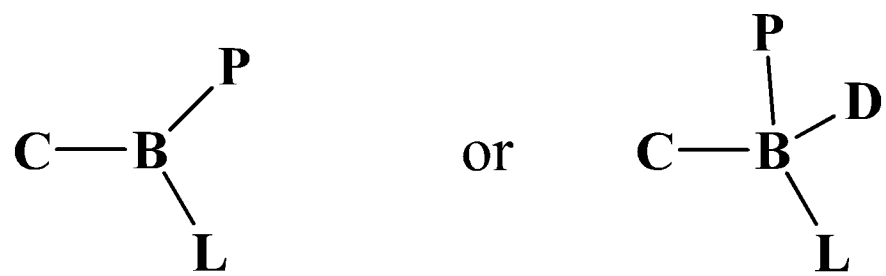
FIG. 1 shows a representation of the conjugates of the present invention.

The present invention is herein disclosed using the following chemical nomenclature:
MAGC-PEGs: monoacylglycerol-carbohydrate-polyethylene glycols
MAPC-PEGs: monoacylpolyamine-carbohydrate-polyethylene glycols
MAAC-PEGs: monoacylamino acid-carbohydrate-polyethylene glycol
ODL-TrpPEGs: oleoyldiethylenetriamine-tryptophanyl PEG
LOS-PEGs: N-lactobionyloleoyl-mPEG serinate
LOS-bioPEGs: N-lactobionyloleoyl-biotinylated PEG serinate
OAPDL-11: oleoyl-N-(3-aminopropyl)propane-1,3-diamine-Undecaethylene glycol methyl ether Lactobionate
GDODL-12: dioleoylglyceroldiethylenetriamine-monomethoxyl dodecaethylene glycol ether lactobionate
GMODL-12: dimyristoylglycerol diethylenetriamine-monomethoxyl dodecaethylene glycol ether lactobionate
GML-12: myristoylglycerol-dodecaethylene glycol lactobionate
GOL-12: oleoylglycerol-dodecaethylene glycol lactobionate
MDTL-12: myristoyldiethylenetetramine-dodecaethylene glycol lactobionate
ODL-12: oleoyldiethylenetriamine-dodecaethylene glycol lactobionate
ODL-15: oleoyldiethylenetriamine-pentadecaethylene glycol lactobionate
ODTL-12: oleoyldiethylenetetramine-dodecaethylene glycol lactobionate
ODTL-15: oleoyldiethylenetetramine-pentadecaethylene glycol lactobionate
MTL-12: myristoyltriethylenetetramine-dodecaethylene glycol lactobionate
OTL-12: oleoyltriethylenetetramine-dodecaethylene glycol lactobionate
OTL-15: oleoyltriethylenetetramine-pentadecaethylene glycol lactobionate
GDODL-12: dioleoylglycerol-diethylenetriamine-monomethoxyl polyethylene glycol ether lactobionate
OAPEL-PEG: oleoyl(aminopropylamino)ethanoyl-mPEG Lactobionate
LOS-bioPEG: N-lactobionyloleoyl-biotinylated PEG Serinate
DCAL-PEG: N-desoxycholylaspartate-mPEG lactobionate
OAL-mPEG: oleoylaminopropanediol-mPEG lactobionate
OAL-bioPEG: oleoylaminopropanediol-biotinylated PEG lactobionate
ODL-ThrPEG: oleoyldiethylenetriamine-threoninyl PEG lactobionate
ODL-bioPEG: oleoyldiethylenetriamine-biotinylated PEG lactobionate
ODL-PEG: oleoyldiethylenetriamine-PEG lactobionate

DETAILED DESCRIPTION OF PREFERRED EMBODIMENTS

Embodiments of the present invention are described herein in the context of varying polymer-carbohydrate-lipid conjugates for drug delivery. Those of ordinary skill in the art will realize that the following detailed description of the present invention is illustrative only and is not intended to be in any way limiting. Other embodiments of the present invention will readily suggest themselves to such skilled persons having the benefit of this disclosure. Reference will now be made in detail to implementation of the present invention.

In the interest of clarity, not all of the routine features of the implementations herein are described. It will be appreciated that in the development of such actual implementation, numerous implementation-specific details must be made in order to achieve the developer's specific goals, and that these specific goals will vary. Though such implementation might be complex, it will still be a routine exercise of engineering.

The invention comprises compounds having a backbone and three appended functional groups: one lipid, one hydrophilic polymer, and one carbohydrate. By combining these three functionalities all into one compound, it is possible to achieve improved formulations of many active agents. The general structure of the family of compounds is shown as FIG. 1, where B indicates the backbone, P indicates the polymer, L indicates the lipid, and C indicates the carbohydrate. In aqueous solutions, the new conjugates act as a solubility enhancer of poor water soluble agents resulting in either a true solution or a very stable emulsified suspension with those of active agents.

Figure 6:
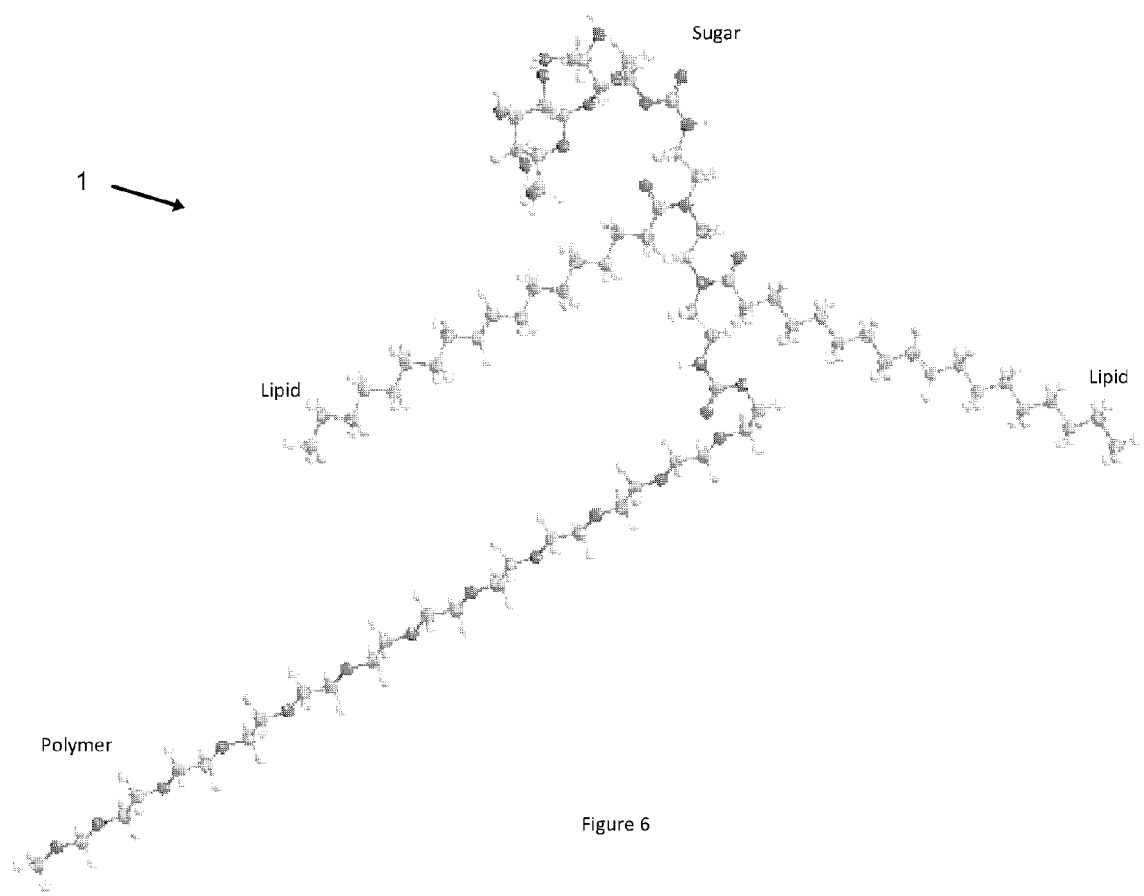
FIG. 6 shows chemical structure 1.

In one aspect, the invention comprises compounds having a backbone and three appended functional groups with four carriers: one or two lipids, one or two hydrophilic polymers, and one or two carbohydrate. By doubling one of these three functionalities all into one compound, it is possible to achieve more enhanced formulations of many poor water soluble or poor permeable active agents. The general structure of the family of compounds is also shown in FIG. 1, where B indicates the backbone, P indicates the polymer, L indicates the lipid, C indicates the carbohydrate, and D as duplicates one of the three carriers. However, the conjugate with four carriers is much bulkier and nonlinear as showed in Chemical Structure 1, in the three-dimensional drawing where the second lipid (as D) is bonded to the central backbone. Chemical Structure 1 is shown in FIG. 6.

Though it is possible to use a variety of hydrophilic polymers in practicing the invention, polyethyleneglycol (PEG) is preferred because of its long history of effectiveness and its status of being generally regarded as safe. Incorporating PEG, the General Structure 1 of the new polymer-carbohydrate-lipids conjugate is:

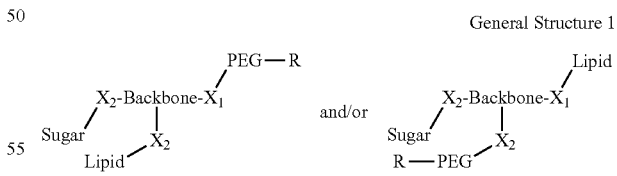

General Structure 1

In General Structure 1, the backbone may be selected from glycerol or glycerol-like analogues, polyamines (tri- or tetra-amines), amino acids having three available binding sites, and triols and triacids such as glucoheptonic acid and tartaric acid. The lipid is selected from fatty acids or bile acids. The carbohydrate is a sugar including monosaccharides or disaccharides or oligosaccharides. $X_1$, $X_2$ and $X_3$ are the same or different linkers. Each linker may be as simple as an oxygen or other single atom. Alternatively, each linker may be single or replicate linkers selected from Table 1 or Table 2. In some cases, the linker may be co-extensive with or a part of the backbone or functional group component used to synthesize the conjugate. Though not shown, the invention also includes compounds in which the carbohydrate is in the center position of the backbone. However, it is more practical to have carbohydrates at the terminus instead of the center of the backbones due to the routes of synthetic chemistry. The general structure is meant to include all racemers or structural isomers of the structure, as they can be functionally equivalent. The PEG chain preferably consists of between about 5 and 45 subunits, and is preferably substantially monodisperse. R is the terminal group on the PEG chain can be selected from a wide variety of chemical moieties. R preferably has a molecular weight of less than about 650.

The terminal group on the PEG chain can be selected from a wide variety of chemical moieties. Such moieties preferably have a molecular weight of less than 650. Such moieties include —$NH_2$, —COOH, —$OCH_2CH_3$, —$OCH_2CH_2OH$, —$COCH=CH_2$, —$OCH_2CH_2NH_2$, —$OSO_2CH_3$, —$OCH_2C_6H_6$, —$OCH_2COCH_2CH_2COONC_4H_4O_2$, —$CH_2CH_2=CH_2$, $C_{10}H_{16}N_2O_3S$ and —$OC_6H_6$. The terminal group may be a functional group that facilitates linking therapeutic or targeting agents to the surface of lipid vesicle aggregates. Amino acids, amino alkyl esters, biotins, maleimide, diglycidyl ether, maleinimido propionate, methylcarbamate, tosylhydrazone salts, azide, propargyl-amine, propargyl alcohol, succinimidyl (NHS) esters (e.g., propargyl NHS ester, NHS-biotin, sulfo-NHS-LC-biotin, or NHS carbonate), hydrazide, succinimidyl ester, succinimidyl tartrate, succinimidyl succinate, and toluenesulfonate salt are useful for such linking. Linked therapeutic and targeting agents may include Fab fragments, cell surface binding agents, and the like. Additionally, the terminal group may include functional cell-targeting ligands such as folate, transferrin and molecules such as monoclonal antibodies, ligands for cellular receptors or specific peptide sequences can be attached to the liposomal surface to provide specific binding sites. The terminal group can be neutral or include either negatively or positively charged head-groups such as decanolamine, octadecylolamine, octanolamine, butanolamine, dodecanolamine, hexanolamine, tetradecanolamine, hexadecanolamine, oleylamine, decanoltrimethylaminium, octadecyloltrimethylaminium, octanoltrimethyl-aminium, butanoltrimethylaminium, dodecanoltrimethylaminium, hexanoltrimethylaminium, tetradecanoltrimethylaminium, hexadecanoltrimethylaminium, oleyltrimethylaminium, for example. Other useful R groups include alkyl groups such as alkoxy moieties, amino acids, and sugars including monosaccharides, disaccharides, trisaccharides and the oligosaccharides—containing 1, 2, 3, and 4 or more monosaccharide units respectively. Additionally, targeting moieties such as antibody fragments and vitamins can also be used as R groups. Generally, the R group is highly soluble in water. The molecular weight of the R group is preferably less than about 650, and for most applications the R group is preferably easily polarized, in order to increase the binding and interaction with proteins at the targeted sites. However, well balanced ionic R groups are advantageously employed for certain modes of administrations such as topical gels and oral solutions targeting the mouth and throat.

Depending on the choice of backbone, functional groups and linkers, the compounds of the invention may be categorized into several classes. These classes include monoacylglycerol-carbohydrate-polyethylene glycols (MAGC-PEGs); monoacyldiethyl-enetetramine-carbohydrate-polyethylene glycols (MADC-PEGs); monoacyltriethyl-enetetramine carbohydrate-polyethylene glycols (MATC-PEGs); monosteroidglycerol-carbohydrate polyethylene glycols (MSGC-PEGs); monosteroid diethylenetetramine-carbohydrate-polyethylene glycols (MSDC-PEGs); and monosteroid triethylenetetramine-carbohydrate polyethylene glycols (MSTC-PEGs).

The present invention includes linking chemical groups that can be selected to optimize and improve PEG-carbohydrate-lipid based formulations. Selecting an appropriate linker between PEG, carbohydrate and backbone can be important for several reasons, as described below.

It is well understood that a drug or compound as a xenobiotic, the normal human body doesn't need it. Ideally, a drug should reach the site of action intact, cure the disease, and leave the body after it completes its mission. However, drug developers often face the dilemma that 70 to 90% of drugs under development have water solubility or permeability problem [Thayer, A M. *Chemical & Engineering News*. 2010; 88, 13-18], so that the drug can not reach its site of action and achieve its therapeutic effect, or too slow, so that it stays in the body for a long time causing side effects. An object of this invention is to develop the polymer-carbohydrate-lipids with unique linkers to help drugs to achieve therapeutic goals.

Xenobiotics follow metabolic processes to be removed from the body. This process most commonly involves cytochrome P450 enzymes. These enzymes are a super family of proteins found in all living organisms. In humans, as well as all other mammalian species, this enzyme system is found principally in the liver but exists in all other organs and tissues. These enzymes catalyze the following reactions: aromatic hydroxylation; aliphatic hydroxylation; N-, O-, and S-dealkylation; N-hydroxylation; N-oxidation; sulfoxidation and deamination. Of particular importance to the present invention are the breakdown processes that the vesicles formed from news lipids, and the new lipids themselves, are expected to undergo. Methoxyl and methylamine groups are expected to undergo demethylation. Amines are expected to undergo N-oxidation or deamination. Sulfur bonds are expected to undergo S-oxidation. Esters and amides are expected to undergo hydrolysis. Since different organs and tissues have differing abilities to perform these different reactions, it is a further objective of the present invention to provide linkers with optimal degradation properties.

Similarly, different microenvironments within the body favor different breakdown processes. For example, acidic gastric fluids favors breakdown of thiol linkages. Therefore, it is still another object of this invention to provide new molecules for designing drug delivery formulations for diverse physiological microenvironments.

Of the three linked PEG, carbohydrate and lipid components, carbohydrate and lipid are digestible by humans while PEG is not. However, as mentioned earlier, PEG is readily excreted. Breaking the linkage among the three components may result in increased clearance for all. It is therefore an object of the invention to use varying biodegradable linkers for optimizing clearance rates of lipid vesicles and lipids used for drug delivery.

Retaining power of lipids can be important in drug formulations and preventing drug precipitation in the body fluids. The present invention provides the means of enhancing retaining power by inclusion carbohydrates into PEG-lipids.

The sugar groups in the conjugates of the invention have larger surface polarity than PEG chains or lipids. Those PEG-carbohydrate-lipid conjugates provide a better drug dispersion for their applications in micro-suspension or nanoparticles, especially for some amphipatic drugs or other compounds; this provides a better equilibrium for the drug or other compounds to partition into the lipid bilayer of the vesicle.

When using existing PEG-lipids such as Capmul®, Centrophase®, Cremophor®, Labrafac®, Labrafil®, Labrasol® and Myverol® for oral liquid formulations, a taste masking agent must be used which may have additional issues for manufacturing processes and costs. PEG-carbohydrate-lipid conjugates generally taste better than PEG-lipids conjugates, and can eliminate the need for taste making agents.

PEG-carbohydate-lipid conjugates can be formulated into injectable preparations free from sugars that are commonly used to stabilize lyophilized proteins and peptides for injectables. Injectables prepared with PEG-carbohydrate-lipid conjugates are very stable even under high temperature and/or high humidity conditions. Reducing or eliminating the use of sugars in pharmaceutical preparation is especially beneficial for patients with diabetes mellitus.

The PEG chains in the conjugates of the present invention are preferably monodisperse. Materials and Methods for synthesizing such monodisperse PEG chains are disclosed in U.S. patent application Ser. No. 12/802,197, which is hereby incorporated by reference in its entirety. Preferably more than 50% of the PEG chains in a particular conjugate have the same molecular weight. More preferably, more than 75% have the same molecular weight. Most preferably, more than 90% have the same molecular weight.

Generally, the invention includes compositions and methods for synthesizing PEG-carbohydrate-lipid conjugates comprising a glycerol or a linear polyamine backbone with one PEG chain and one carbohydrate group and one lipid group bonded to the backbone. Selected linkers can be used as spacers between the backbone and the PEG chain or the carbohydrate or the lipid group.

Variations of the invention include a variety of compounds as for the backbone with at least three available binding positions. Molecules having two available binding positions, such as ethylenediamine, diaminopropane, ethanolamine, and aminopropanol, can be chemically extended to three binding sites.

Commercially available glycerol lipid monoesters may be used to formulate many compounds by linking new moieties to the available positions on the glycerol backbone. While positional isomers may be produced during synthesis, such isomers may be functionally equivalent. However, the choice of isomer may have implications in a variety of delivery process such as intracellular transport of lipophilic molecules as well as their use as vehicles in pharmaceutical applications. For example, isomers may differ in the ability to stabilize a compound during solubilizing and storage.

Table 1 describes amino acid linkers ("X") useful in practicing the invention.

TABLE 1

Amino Acid Linkers

| No | Amino Acid | Side chain charge at pH 7.4[a] |
|----|------------|-------------------------------|
| 1 | Alanine | Neutral |
| 2 | Arginine | Positive |
| 3 | Asparagine | Neutral |
| 4 | Aspartic acid | Negative |
| 5 | Cysteine | Neutral |
| 6 | Glutamic acid | Negative |
| 7 | Glutamine | Neutral |
| 8 | Glycine | Neutral |
| 9 | Histidine | Positive/neutral |
| 10 | Isoleucine | Neutral |

TABLE 1-continued

Amino Acid Linkers

| No | Amino Acid | Side chain charge at pH 7.4[a] |
|----|------------|-------------------------------|
| 11 | Leucine | Neutral |
| 12 | Lysine | Positive |
| 13 | Methionine | Neutral |
| 14 | Phenylalanine | Neutral |
| 15 | Proline | Neutral |
| 16 | Serine | Neutral |
| 17 | Threonine | Neutral |
| 18 | Tryptophan | Neutral |
| 19 | Tyrosine | Neutral |
| 20 | Valine | Neutral |

Hausman, Robert E.; Cooper, Geoffrey M. (2004). The cell: a molecular approach. Washington, D.C: ASM Press. p. 51

In additional these standard amino acid linkers listed in Table 1, the present invention also includes nonstandard amino acid backbones such as beta-amino acids, lanthionine, Ornithine, 2-aminoisobutyric acid, dehydroalanine, selenocysteine, and gamma-aminobutyric acid.

Preferable amino acid linkers are Proline, Glycine, Alanine, Lysine, Cysteine, Valine, Isoleucine, Leucine, Methionine, Phenylalanine, Histidine, Tryptophan, Tyrosine, Selenocysteine, and Arginine, more preferable are Proline, Glycine, Alanine, Lysine, Cysteine, Valine, Isoleucine, Leucine, Methionine, most preferable are Proline, Glycine, Alanine and Lysine.

Conjugates of the present invention may comprise the linkers as listed in Table 2. The structures shown in the table were mainly named by ChemDraw (CambridgeSoft, Cambridge, Mass., USA). In the event of minor variations of chemical names, the structures shown are meant to be controlling.

TABLE 2

Other linkers use in the invention

| No | Symbol | Linker |
|----|--------|--------|
| 1 | $N_1$ | 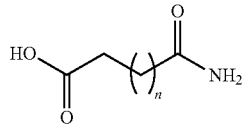<br>n = 1 to 18, carbamoyl-carboxylic acid |
| 2 | $N_2$ | 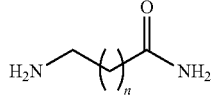<br>n = 1 to 18: n-amino-alkyl-amide |
| 3 | $N_3$ | 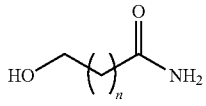<br>n = 1 to 18: n-hydroxyl-alkyl-amide |
| 7 | $N_7$ | 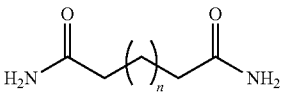<br>n = 1 to 18, alkyl diamide |

TABLE 2-continued

Other linkers use in the invention

| No | Symbol | Linker |
|---|---|---|
| 8 | $N_8$ | $H_2N-(-)_n-CH(NH_2)-COOH$ <br> n = 1 to 18, diamino-carboxylic acid |
| 9 | $N_9$ | $HO-(-)_n-NH_2$ <br> n = 2 to 18: n-aminoalcohol |
| 10 | $N_{10}$ | $H_2N-(-)_n-NH_2$ <br> n = 2 to 18: diamine |
| 11 | $N_{11}$ | $HO-C(O)-NH-(-)_n-NH_2$ <br> n = 1 to 18: n-amino-alkyl-carbamic acid |
| 12 | $N_{12}$ | $H_2N-C(O)-(-)-S-(-)_n-NH_2$ <br> n = 1 to 12: n-amino(methyl-thio)$_n$-propanamide |
| 13 | $S_1$ | $HS-(-)_n-COOH$ <br> n = 1 to 18: n-mercaptocarboxylic acid |
| 14 | $S_2$ | $HS-(-)_n-CH(NH_2)-COOH$ <br> n = 1 to 18: n-mercapto-alpha-aminocarboxylic acid |
| 15 | $S_3$ | $HO-C(O)-NH-(-)_n-SH$ <br> n = 1 to 18: n-mercapto-alkyl-carbamic acid |
| 16 | $S_4$ | $HO-C(O)-CH(R)-S-(-)_n-SH$ <br> R = H or Alkyl group, n = 0 to 18 |
| 17 | $S_5$ | $HO-C(O)-CH(R)-S-CH(OH)-(-)_n-CH(OH)-CH_2-SH$ <br> R = H or Alkyl group <br> n = 0 to 12: n-mercaptopropylthio)carboxylic acid |
| 18 | $S_6$ | $HS-(-)_n-NH_2$ <br> n = 1 to 18: Amino-thiol |
| 19 | $S_7$ | $HS-(-)_n-OH$ <br> n = 1 to 18: n-mercapto-alcohol |
| 20 | $S_8$ | $HS-(-)_n-SH$ <br> n = 1 to 18: dithiol |
| 21 | $S_9$ | $HO-C(O)-(-)-S-(-)_n-NH_2$ <br> n = 1 to 18: n-amino-(methyl-thio)$_n$-propanoic acid |
| 22 | $Ac_1$ | $HO-(-)_n-COOH$ <br> n = 1 to 18: n-hydroxy-carboxylic acid |
| 23 | $Ac_2$ | $H_2N-(-)_n-COOH$ <br> n = 1 to 18: n-amino-carboxylic acid |
| 24 | $Ac_3$ | $HO-C(O)-(-)_n-COOH$ <br> n = 1 to 18: di-carboxylic acid, n = 1: succinyl |
| 25 | $Ac_4$ | $HO-(-)_n-OH$ <br> n = 1 to 18; diols |
| 26 | $Ac_5$ | $HO-C(O)-NH-(-)_n-OH$ <br> n = 1 to 18: n-hydroxy-alkyl-carbamic acid |

TABLE 2-continued

Other linkers use in the invention

| No | Symbol | Linker |
|----|--------|--------|
| 27 | Ac$_6$ | HO-C(=O)-CH$_2$-CH(S-)-(CH$_2$)$_n$-OH | n = 1 to 18: n-hydroxyl-(methyl-thio)$_n$-propanoic acid

In this aspect of the invention, X may comprise one or more carbon atoms in addition to the linker. The linker is preferably oriented so that the backbone is coupling to the three carrier groups.

The present invention can be practiced using a wide variety of central backbones. Preferable backbones have at least three available positions for carbohydrate or lipid or PEG attachments through esterification or etherification. For those suitable molecules can be used as the backbone including glycerol or glycerol-like analogues or linear amines or amino acids or triols or diols with a carboxy group or amine, and diamines with a hydroxyl or carboxy group. More preferable the space between the two closest binding positions on the backbone is between 2 to 8 elements such as single carbon or CH$_2$. Most preferable space between the two closest binding positions on the backbone is between 2 and 4 elements.

For those glycerol or glyceride or triols or triacids or tetracids or aminodiols and analogues are suitable to be used as the central backbone including and not limited to 3-amino-1,2-propanediol, 3-bromo-1,2-propanediol, 3-chloro-1,2-propanediol, 3-fluoro-1,2-propanediol, DL-glyceric acid, diamino-propionic acid, tartaric acid, glucoheptonic acid and, 2,4-butanetriol, 2,2-bis(hydroxymethyl)-butyric acid, 1,3-Diamino-2-propanol and 2-(3-Aminopropylamino)-ethanol, 3-amino-1,2-propanediol, 3-bromo-1,2-propanediol, 3-chloro-1,2-propanediol, 3-fluoro-1,2-pro- For those amines are suitable to be used as the central backbones including and not limited to diethylenetriamine, spermidine, triethylenetetramine, spermine, norspermidine, bis(3-aminopropyl)-1,3-propanediamine, bis(hexamethylene)triamine, diethylenetriamine, bis(3-aminopropyl)amine, triethylenetetramine, tris(2-aminoethyl)amine, spermine, spermidine, norspermidine, bis(3-aminopropyl)-1,3-propanediamine, 1,2-bis(3-aminopropylamino)ethane, N,N'-bis (3-aminopropyl)-1,3-propanediamine, tris(hydroxymethyl) aminomethane, diaminobenzidine, N-ethyl-N'-(3-dimethylaminopropyl)carbodiimide.

For those amino acids with two carboxyl groups or two hydroxyl or two amino groups can be used as the central backbone, preferable amino acids are Aspartic Acid, Glutamic Acid, Asparagine, Glutamine, Ornithine, Serine and Threonine, more preferable are Aspartic Acid, Glutamic Acid, Ornithine, Serine and Threonine, and most preferable are Aspartic Acid, Glutamic Acid, Ornithine and Serine.

The invention can be practiced using a wide variety of fatty acids or those of diacylglycerols consisting of two fatty acids. Table 3 lists some saturated lipids for use in the invention. Table 4 lists some unsaturated lipids for use in the invention.

TABLE 3

Saturated lipids for use in the invention:

| Common name | IUPAC name | Chemical structure | Abbr. | Melting point (° C.) |
|---|---|---|---|---|
| Butyric | Butanoic acid | CH$_3$(CH$_2$)$_2$COOH | C4:0 | −8 |
| Caproic | Hexanoic acid | CH$_3$(CH$_2$)$_4$COOH | C6:0 | −3 |
| Caprylic | Octanoic acid | CH$_3$(CH$_2$)$_6$COOH | C8:0 | 16-17 |
| Capric | Decanoic acid | CH$_3$(CH$_2$)$_8$COOH | C10:0 | 31 |
| Lauric | Dodecanoic acid | CH$_3$(CH$_2$)$_{10}$COOH | C12:0 | 44-46 |
| Myristic | Tetradecanoic acid | CH$_3$(CH$_2$)$_{12}$COOH | C14:0 | 58.8 |
| Palmitic | Hexadecanoic acid | CH$_3$(CH$_2$)$_{14}$COOH | C16:0 | 63-64 |
| Stearic | Octadecanoic acid | CH$_3$(CH$_2$)$_{16}$COOH | C18:0 | 69.9 |
| Arachidic | Eicosanoic acid | CH$_3$(CH$_2$)$_{18}$COOH | C20:0 | 75.5 |
| Behenic | Docosanoic acid | CH$_3$(CH$_2$)$_{20}$COOH | C22:0 | 74-78 |

TABLE 4

Unsaturated lipids

| Name | Chemical structure | $\Delta^x$ Location of double bond | # carbon/ double bonds |
|---|---|---|---|
| Myristoleic acid | CH$_3$(CH$_2$)$_3$CH=CH(CH$_2$)$_7$COOH | cis-$\Delta^9$ | 14:1 |
| Palmitoleic acid | CH$_3$(CH$_2$)$_5$CH=CH(CH$_2$)$_7$COOH | cis-$\Delta^9$ | 16:1 |
| Oleic acid | CH$_3$(CH$_2$)$_7$CH=CH(CH$_2$)$_7$COOH | cis-$\Delta^9$ | 18:1 |
| Linoleic acid | CH$_3$(CH$_2$)$_4$CH=CHCH$_2$CH=CH(CH$_2$)$_7$COOH | cis,cis-$\Delta^9,\Delta^{12}$ | 18:2 |
| α-Linolenic acid | CH$_3$CH$_2$CH=CHCH$_2$CH=CHCH$_2$CH=CH(CH$_2$)$_7$COOH | cis,cis,cis-$\Delta^9,\Delta^{12},\Delta^{15}$ | 18:3 |
| Arachidonic acid | CH$_3$(CH$_2$)$_4$CH=CHCH$_2$CH=CHCH$_2$CH=CHCH$_2$CH=CH(CH$_2$)$_3$COOH$^{NIST}$ | cis,cis,cis,cis-$\Delta^5,\Delta^8,\Delta^{11},\Delta^{14}$ | 20:4 |
| Erucic acid | CH$_3$(CH$_2$)$_7$CH=CH(CH$_2$)$_{11}$COOH | cis-$\Delta^{13}$ | 22:1 | panediol, DL-glyceric acid, diaminopropionic acid, tartaric acid, glucoheptonic acid and, 2,4-butanetriol, 2,2-bis(hydroxymethyl)butyric acid, 1,3-Diamino-2-propanol, 2-(3-aminopropylamino)-ethanol, and 3-((3-aminopropyl)-amino)propanol, threitol, meso-erythritol, dithiothreitol, trimethylcyclohexane-1,3,5-tricarboxylic acid, trimethylbis (hexamethylene)triamine, bis(hexamethylene)triamine, arginine, oxylyldiamino-propionic acid having three or four available binding positions or sites, triols, triacids, glucoheptonic acid, triazacyclononane, tetraaza-cyclododecane, and tartaric acid.

Suitable lipids for synthesis of PEG-carbohydrate-lipid conjugates include bile acids (steroid acids) as well as alkyl chains. Therefore, the present invention includes a variety of PEG-carbohydrate-lipid conjugates and the steroid acid-carbohydrate-PEG conjugates can be incorporated into liposomes as a targeting moiety for lipid-based drug delivery to specific cells or as self-emulsifying drug delivery systems (SEDDS).

Bile acids (steroid acids) constitute a large family of molecules, composed of a steroid structure with four rings, a five or eight carbon side-chain terminating in a carboxylic acid, and the presence and orientation of different numbers of hydroxyl groups. The four rings are labeled from left to right A, B, C, and D, with the D-ring being smaller by one carbon than the other three. An exemplary bile acid is shown in Chemical Structure 2. All bile acids have side chains. When subtending a carboxyl group that can be amide-linked with taurine or glycine, the nuclear hydroxyl groups can be esterified with glucuronide or sulfate which are essential for the formation of water soluble bile salts from bile alcohols.

Chemical Structure 2

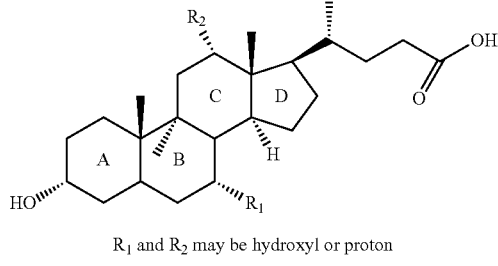

R₁ and R₂ may be hydroxyl or proton

The new steroid-carbohydrate-PEGs is bile acid including and not limited to cholic acid, desoxycholic acid, dehydrocholic acid, glycochenodeoxycholic acid and glycodeoxycholic acid and the invention can be practiced using a wide variety of bile acids as listed in Table 5 and a steroid-carbohydrate-PEG is meant to include all racemers and structural isomers of the structure, as they can be functionally equivalent.

TABLE 5

Bile acid (steroid acid) and its analogues for use in the Invention

| Name | Other Name |
|---|---|
| Cholic acid | 3α,7α,12α-trihydroxy-5β-cholanoic acid |
| Desoxycholic acid | 3α,12α-Dihydroxy-5β-cholanic acid |
| 5-Cholenic acid-3β-ol | 3β-Hydroxy-5-cholen-24-oic acid |
| Dehydrocholic acid | 3,7,12-Trioxo-5β-cholanic acid |
| Glycocholic acid | N-(3α,7α,12α-Trihydroxy-24-oxocholan-24-yl)-glycine |
| Glycodeoxycholic acid | N-(3α,12α-Dihydroxy-24-oxocholan-24-yl)glycine |
| Chenodeoxycholic acid | 3α,7α-dihydroxy-5β-cholanic acid |
| Glycochenodeoxycholic acid | N-(3α,7α-Dihydroxy-24-oxocholan-24-yl)glycine |
| Ursodeoxycholic acid | Ursodiol |
| Lithocholic acid | 3α-Hydroxy-5β-cholan-24-oic acid |
| Hyodeoxycholic acid | 3α,6α-Dihydroxy-5β-cholan-24-oic acid |
| 5β-Cholanic acid-3,7-dione | 3,7-Diketo-5β-cholan-24-oic acid |

Currently only a few modifications in structure have been studied with respect to the physical-chemical properties of bile salts. One patent publication (WO 02083147) discloses bile salt fatty acid conjugate in which a bile acid or bile salt is conjugated in position 24 (carboxyl) with a suitable amino acid, and the unsaturated C=C bond is conjugated with one or two fatty acid radicals having 14-22 carbon atoms. That conjugate is intended to be used as a pharmaceutical composition for the reduction of cholesterol in blood, for the treatment of fatty liver, hyperglycemia and diabetes. Another patent (US 2003212051) discloses acyclovir-bile acid prodrugs in which a linker group may be used between the bile acid and the compound.

Suitable carbohydrates for the Lipid-carbohydrate-PEG conjugates include monosaccharides or disaccharides or oligosaccharides as listed in Table 6.

TABLE 6

Carbohydrates for use in the Invention

| Monosaccharide | trioses | ketotriose (dihydroxyacetone)•aldotriose (glyceraldehyde) |
|---|---|---|
| | tetroses | ketotetrose (erythrulose)•aldotetroses (erythrose, threose) |
| | pentoses | ketopentose (ribulose, xylulose), aldopentose (ribose, arabinose, xylose, lyxose), deoxy carbohydrate (deoxyribose) |
| | hexoses | ketohexose (psicose, fructose, sorbose, tagatose), aldohexose (allose, altrose, glucose, mannose, gulose, idose, galactose, talose), deoxy carbohydrate (fucose, fuculose, rhamnose) |
| | others | heptose (sedoheptulose)•octose•nonose (neuraminic acid) |
| Multiple | disaccharides | sucrose, lactose, maltose, trehalose, turanose, cellobiose |
| | trisaccharides | raffinose, melezitose, maltotriose |
| | tetrasaccharides | acarbose, stachyose |
| | other oligosaccharides | fructooligosaccharide (FOS), galacto-oligosaccharides (GOS), mannan-oligosaccharides (MOS) |
| | polysaccharides | n-acetylglucosamine, chitin, |

The lipid-carbohydrate-PEG conjugates of the present invention may be used for many applications. Formulation and delivery of pharmaceutical and cosmetic agents have been described. Additionally, the Lipid-carbohydrate-PEGs of the present invention may be used in other contexts where water soluble lipids are advantages, for example industrial and food processes.

The syntheses used in this invention to form monoacylglycerol-carbohydrate-polyethyleneglycols generally utilizes the reaction of the PEG polymer with a linker that is reactive with hydroxyl groups, typically anhydrides, acid chlorides, chloroformates and carbonates, aldehyde, esters, amides etc ore more efficient functional groups for the conjugation. Preferred end groups include maleimide, vinyl sulfones, pyridyl disulfide, amine, carboxylic acids and succinimidyl (NHS) esters.

In another aspect the invention includes a PEG-carbohydrate-lipid conjugate having the General Structure 3:

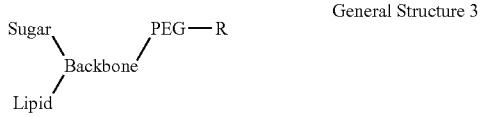

General Structure 3 where the backbone is selected from glycerol or glycerol-like analogues or linear amines (tri- or tetra-amines) or amino acids having three available binding sites; where the lipid is selected from carboxylic acids including and not limited to diacylglycerols or fatty acids or bile acids; sugar is a carbohydrate including monosaccharides or disaccharides or oligosaccharides; where the three substitutable groups are covalently bond to the backbone through a etherification or esterification or amidification or similar substitution reactions. The General Structure is meant to include all racemers or structural isomers of the structure, as they can be functionally equivalent. Where the PEG chain may consist of between about 5 and 45 subunits. Where R is the terminal group on the PEG chain can be selected from a wide variety of chemical moieties. R preferably has a molecular weight of less than about 650. The PEG-carbohydrate-lipid conjugates are useful for applications other than liposomes, e.g., as a solvent.

Synthesis of the new lipids may be controlled so that there is a single linker in each Lipid-carbohydrate-PEG molecule. In some situations, however, it may be useful to have multiple copies of the same linker, or combinations of different linkers in a single molecule as the following General Structure 4:

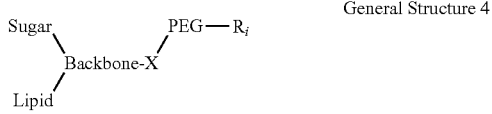

General Structure 4 where lipid is an alkyl group having between 4 and 22 carbons (Tables 3 and 4) or bile acids (Table 5) having a particular steroid structure of 24 carbons; where sugar is a carbohydrate including monosaccharides or disaccharides or oligosaccharides (Table 6); and where X is one or more linkers selected from the Table 1 or 2 or groups consisting of oxy, amino acids, amino, succinylamino, acetamido, aminopentanamido, aminoacetyl, thiopropanoayl, N-(mercaptomethyl)propionamido, mercaptopropylthio)-propanoyl, (1,2-dihydroxy-3-mercaptopropylthio)propanoyl, succinyl, acetyl, oxopentanoyl, carbamoyl, aminoalkyl, glutaramido, aminoethanethiol, mercaptopropanol, (hydroxypropylthio)-propanoayl, 3-((2-propionamidoethyl)disulfanyl)propanoayl, (((acetamidoethyl)disulfanyl)-propanoyloxy)glutaramido, aminoethanethioate, and 2-hydroxyacetic proprionic anhydride.

In one aspect the invention includes a PEG-carbohydrate-lipid conjugate represented by the following General Structure 5:

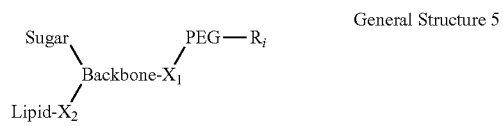

General Structure 5 where lipid is a diacylglycerol or a alkyl group having between 4 and 22 carbons (Table 3 and 4) or bile acids having a particular steroid structure of 24 carbons (Table 5); where carbohydrate is a carbohydrate including monosaccharides or disaccharides or oligosaccharides; and where $X_1$ and $X_2$ are the same or different linkers that consist of one or more linkers selected from the Table 1 or 2 or the group of oxy, amino, succinylamino, acetamido, aminopentanamido, aminoacetyl, thiopropanoayl, N-(mercaptomethyl)-propionamido, mercaptopropylthio)-propanoyl, (1,2-dihydroxy-3-mercaptopropylthio)-propanoyl, succinyl, acetyl, oxopentanoyl, carbamoyl, aminoalkyl, glutaramido, aminoethanethiol, mercaptopropanol, (hydroxypropylthio)propanoayl, 3-((2-propionamidoethyl)disulfanyl)propanoayl, (((acetamidoethyl)disulfanyl)propanoyloxy)-glutaramido, aminoethanethioate, and 2-hydroxyacetic proprionic anhydride. More preferably $R_i$ has a molecular weight of less than about 650. Fatty acid may preferably be selected from the group consisting of oleate, myristate, linoleate and palmitate. Sugar may preferably be selected from Table 6, the group consisting of aldose, ketose, pyranose, furanose, trioses, tetroses, pentoses, hexoses, sucrose, lactose, maltose, trehalose, turanose, cellobiose, raffinose, melezitose, maltotriose, acarbose, stachyose. The PEG chain may consist of between about 6 and 45 subunits. More preferably the PEG chain consists of between about 8 and 24 subunits. Still more preferably the PEG chain consists of between about 12 and 24 subunits.

In another aspect the invention includes a compound represented by the following General Structure 6:

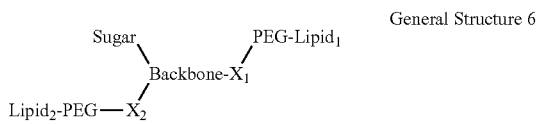

General Structure 6 where $Lipid_1$ and $Lipid_2$ may be the same or different alkyl groups having between 4 and 22 carbons (Tables 3 and 4) or bile acids having a particular steroid structure of 24 carbons (Table 5); and where sugar is a carbohydrate selected from Table 6, the group consists of aldose, ketose, pyranose, furanose, trioses, tetroses, pentoses, hexoses, sucrose, lactose, maltose, trehalose, turanose, cellobiose, raffinose, melezitose, maltotriose, acarbose, stachyose. where $X_1$ and $X_2$ may be the same or different linkers that consist of one or more linkers selected from the Table 1 or 2 or the group of oxy, amino, succinylamino, acetamido, aminopentanamido, aminoacetyl, thiopropanoayl, N-(mercaptomethyl)propionamido, mercaptopropylthio)-propanoyl, (1,2-dihydroxy-3-mercaptopropylthio)propanoyl, succinyl, acetyl, oxopentanoyl, carbamoyl, aminoalkyl, glutaramido, aminoethanethiol, mercaptopropanol, (hydroxypropylthio)propanoayl, 3-((2-propionamidoethyl)-disulfanyl)propanoayl, (((acetamidoethyl)disulfanyl)propanoyloxy)-glutaramido, aminoethanethioate, and 2-hydroxyacetic proprionic anhydride. $Lipid_1$ and $Lipid_2$ may preferably be selected from the group consists of oleate, myristate, linoleate and palmitate. The PEG chain may consist of between about 3 and 45 subunits. More preferably the PEG chain consists of between about 4 and 24 subunits. Still more preferably the PEG chain consists of between about 4 and 12 subunits.

In another aspect the invention includes a molecule comprising a compound represented by the following General Structure 7:

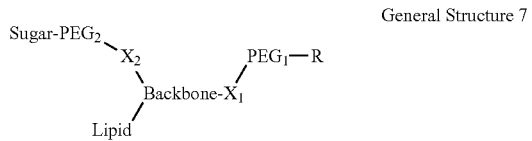

General Structure 7 where sugar is a carbohydrate selected from Table 6, the group consists of aldose, ketose, pyranose, furanose, trioses, tetroses, pentoses, hexoses, sucrose, lactose, maltose, trehalose, turanose, cellobiose, raffinose, melezitose, maltotriose, acarbose, stachyose; and where lipid is a diacylglycerol or a fatty acid from alkyl groups (Tables 3 & 4) having between 4 and 22 carbons or bile acids having a particular steroid structure of 24 carbons (Table 5); where $X_1$ and $X_2$ may be same or different linkers selected from Table 1 or 2 or a group consisting of oxy, amino, succinylamino, acetamido, aminopentanamido, aminoacetyl, thiopropanoayl, N-(mercaptomethyl)propionamido, mercaptopropylthio)-propanoyl, (1,2-dihydroxy-3-mercaptopropylthio)propanoyl, succinyl, acetyl, oxopentanoyl, carbamoyl, aminoalkyl, glutaramido, aminoethanethiol, mercaptopropanol, (hydroxypropylthio)-propanoayl, 3-((2-propionamidoethyl)-disulfanyl)propanoayl, (((acetamidoethyl)disulfanyl)-propanoyloxy)-glutaramido, aminoethanethioate, and 2-hydroxyacetic proprionic anhydride. More preferably $R_i$ has a molecular weight of less than about 650. Lipid may preferably be selected from diacylglycerols or a fatty acid the group consisting of oleate, myristate, linoleate and palmitate. $PEG_1$ and $PEG_2$ may have the same or a different number of subunits. The PEG chain may consist of between about 3 and 45 subunits. More preferably the PEG chain consists of between about 4 and 24 subunits. Still more preferably the PEG chain consists of between about 4 and 12 subunits.

In another aspect the invention includes a molecule comprising a compound represented by the following General Structure 8:

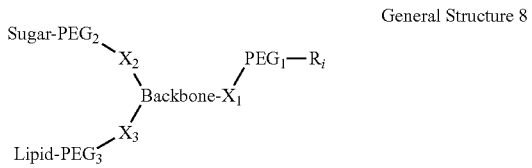

General Structure 8 where sugar is a carbohydrate selected from Table 6, the group consists of aldose, ketose, pyranose, furanose, trioses, tetroses, pentoses, hexoses, sucrose, lactose, maltose, trehalose, turanose, cellobiose, raffinose, melezitose, maltotriose, acarbose, stachyose; and where lipid is selected from alkyl groups (Tables 3 and 4) having between 4 and 22 carbons or bile acids having a particular steroid structure of 24 carbons (Table 5); and where $X_1$, $X_2$ and $X_3$ are the same or different linkers selected from Table 1 or 2 or a group consisting of one or more linkers selected from oxy, amino, succinylamino, acetamido, aminopentanamido, aminoacetyl, thiopropanoayl, N-(mercaptomethyl)propionamido, mercaptopylthio)propanoyl, (1,2-dihydroxy-3-mercaptopropylthio)propanoyl, succinyl, acetyl, oxopentanoyl, carbamoyl, aminoalkyl, glutaramido, aminoethanethiol, mercaptopropanol, (hydroxypropylthio)propanoayl, 3-((2-propionamidoethyl)disulfanyl)propanoayl, (((acetamidoethyl)-disulfanyl)propanoyloxy)-glutaramido, aminoethanethioate, and 2-hydroxyacetic proprionic anhydride. More preferably $R_i$ has a molecular weight of less than about 650. $R_i$ may be either —OH or —OCH$_3$. The lipid may preferably be selected from diacylglycerols or the group consisting of oleate, myristate, linoleate and palmitate. $PEG_1$, $PEG_2$ and $PEG_3$ may have the same or a different number of subunits. The PEG chain may consist of between about 3 and 45 subunits. More preferably the PEG chain consists of between about 3 and 24 subunits. Still more preferably the PEG chain consists of between about 4 and 12 subunits.

In another aspect the invention includes a molecule comprising a compound represented by the following General Structure 9:

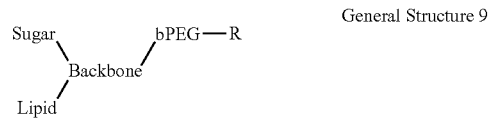

General Structure 9

Where the backbone is selected from glycerol or glycerol-like analogues or linear amines (tri- or tetra-amines) or amino acids having three available binding sites; where the lipid is selected from diacylglycerols or carboxylic acids including and not limited to fatty acids or bile acids; sugar is a carbohydrate including monosaccharides or disaccharides or oligosaccharides; where the three substitutable groups are covalently bond to the backbone through a etherification or esterification or amidification or similar substitution reactions. The General Structure is meant to include all racemers or structural isomers of the structure, as they can be functionally equivalent. Where the bPEG is a branched PEG with 2 or more PEG chains and each PEG chain may consist of between about 5 and 45 subunits. Where R is the terminal group on each PEG chain which may be the same or different and that can be selected from a wide variety of chemical moieties. R preferably has a molecular weight of less than about 650. The PEG-carbohydrate-lipid conjugates are useful for applications other than liposomes, e.g., as a solvent.

In another aspect the invention includes a PEG-carbohydrate-lipid conjugate having the General Structure 10:

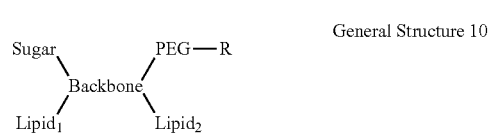

General Structure 10 where Lipid1 and Lipid2 may be the same or different alkyl groups having between 4 and 22 carbons (Table 3 and 4) or bile acids having a particular steroid structure of 24 carbons (Table 5); where the backbone is selected from polyamines or compounds having four available binding sites; where the lipid is selected from carboxylic acids including and not limited to diacylglycerols or fatty acids or bile acids; sugar is a carbohydrate including monosaccharides or disaccharides or oligosaccharides; where the three substitutable groups are covalently bond to the backbone through a etherification or esterification or amidification or similar substitution reactions. The General Structure is meant to include all racemers or structural isomers of the structure, as they can be functionally equivalent. Where the PEG chain may consist of between about 5 and 45 subunits. Where R is the terminal group on the PEG chain can be selected from a wide variety of chemical moieties. R preferably has a molecular weight of less than about 650. The PEG-carbohydrate-lipid conjugates are useful for applications other than liposomes, e.g., as a solvent.

Similarly to the three carrier conjugates, synthesis of the new lipids may be controlled so that there is a single linker in each Lipid-carbohydrate-PEG molecule. In some situations, however, it may be useful to have multiple copies of the same linker, or combinations of different linkers in a single molecule as the following General Structure 11:

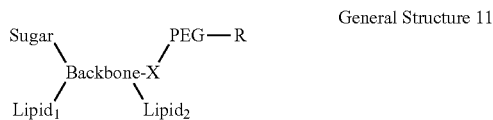

General Structure 11 where $Lipid_1$ and $Lipid_2$ may be the same or different alkyl groups having between 4 and 22 carbons (Table 3 and 4) or bile acids having a particular steroid structure of 24 carbons (Table 5); where sugar is a carbohydrate including monosaccharides or disaccharides or oligosaccharides (Table 6); and where X is one or more linkers selected from the Table 1 or 2 or groups consisting of oxy, amino acids, amino, succinylamino, acetamido, aminopentanamido, aminoacetyl, thiopropanoayl, N-(mercaptomethyl)propionamido, mercaptopropylthio)-propanoyl, (1,2-dihydroxy-3-mercaptopropylthio)propanoyl, succinyl, acetyl, oxopentanoyl, carbamoyl, aminoalkyl, glutaramido, aminoethanethiol, mercaptopropanol, (hydroxypropylthio)-propanoayl, 3-((2-propionamidoethyl)disulfanyl)-propanoayl, (((acetamidoethyl)disulfanyl)-propanoyloxy)-glutaramido, aminoethanethioate, and 2-hydroxyacetic proprionic anhydride.

In one aspect the invention includes a PEG-carbohydrate-lipid conjugate represented by the following General Structure 12:

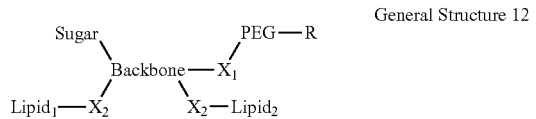

General Structure 12 where $Lipid_1$ and $Lipid_2$ may be the same or different alkyl groups having between 4 and 22 carbons (Table 3 and 4) or bile acids having a particular steroid structure of 24 carbons (Table 5); where carbohydrate is a carbohydrate including monosaccharides or disaccharides or oligosaccharides; and where $X_1$ and $X_2$ are the same or different linkers that consist of one or more linkers selected from the Table 1 or 2 or the group of oxy, amino, succinylamino, acetamido, aminopentanamido, aminoacetyl, thiopropanoayl, N-(mercaptomethyl)-propionamido, mercaptopropylthio)-propanoyl, (1,2-dihydroxy-3-mercaptopropylthio)-propanoyl, succinyl, acetyl, oxopentanoyl, carbamoyl, aminoalkyl, glutaramido, aminoethanethiol, mercaptopropanol, (hydroxypropylthio) propanoayl, 3-((2-propionamidoethyl)disulfanyl)propanoayl, (((acetamidoethyl)disulfanyl)propanoyloxy)-glutaramido, aminoethanethioate, and 2-hydroxyacetic proprionic anhydride. More preferably R has a molecular weight of less than about 650. $Lipid_1$ and $Lipid_2$ are the same or different. Fatty acid may preferably be selected from the group consisting of oleate, myristate, linoleate and palmitate. Sugar may preferably be selected from Table 6, the group consisting of aldose, ketose, pyranose, furanose, trioses, tetroses, pentoses, hexoses, sucrose, lactose, maltose, trehalose, turanose, cellobiose, raffinose, melezitose, maltotriose, acarbose, stachyose. The PEG chain may consist of between about 6 and 45 subunits. More preferably the PEG chain consists of between about 8 and 24 subunits. Still more preferably the PEG chain consists of between about 12 and 24 subunits.

In another aspect the invention includes a compound represented by the following General Structure 13:

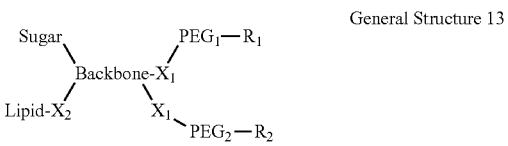

General Structure 13 where $PEG_1$ and $PEG_2$ may have the same or a different number of subunits, and where lipid is a diacylglycerol or a fatty acid from alkyl groups (Tables 3 & 4) having between 4 and 22 carbons or bile acids having a particular steroid structure of 24 carbons (Table 5); where sugar is a carbohydrate selected from Table 6, the group consists of aldose, ketose, pyranose, furanose, trioses, tetroses, pentoses, hexoses, sucrose, lactose, maltose, trehalose, turanose, cellobiose, raffinose, melezitose, maltotriose, acarbose, stachyose, where $X_1$ and $X_2$ may be the same or different linkers that consist of one or more linkers selected from the Table 1 or 2 or the group of oxy, amino, succinylamino, acetamido, aminopentanamido, aminoacetyl, thiopropanoayl, N-(mercaptomethyl)propionamido, mercaptopropylthio)-propanoyl, (1,2-dihydroxy-3-mercaptopropylthio)propanoyl, succinyl, acetyl, oxopentanoyl, carbamoyl, aminoalkyl, glutaramido, aminoethanethiol, mercaptopropanol, (hydroxypropylthio)-propanoayl, 3-((2-propionamidoethyl)-disulfanyl)propanoayl, (((acetamidoethyl)disulfanyl)-propanoyloxy)-glutaramido, aminoethanethioate, and 2-hydroxyacetic proprionic anhydride. Lipid may preferably be selected from the group consists of oleate, myristate, linoleate and palmitate. The PEG chains may consist of between about 4 and 45 subunits. More preferably the PEG chain consists of between about 4 and 24 subunits. Still more preferably the PEG chain consists of between about 8 and 16 subunits. $R_1$ and $R_2$ on each PEG chain which may be the same or different terminal group having a molecular weight of less than about 650.

In another aspect the invention includes a molecule comprising a compound represented by the following General Structure 14:

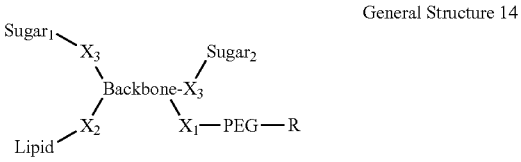

General Structure 14 where Sugar₁ and Sugar₂ may be the same or different carbohydrate selected from Table 6, the group consists of aldose, ketose, pyranose, furanose, trioses, tetroses, pentoses, hexoses, sucrose, lactose, maltose, trehalose, turanose, cellobiose, raffinose, melezitose, maltotriose, acarbose, stachyose; and where lipid is a diacylglycerol or a fatty acid from alkyl groups (Tables 3 & 4) having between 4 and 22 carbons or bile acids having a particular steroid structure of 24 carbons (Table 5); where $X_1$, $X_2$ and $X_3$ may be same or different linkers selected from Table 1 or 2 or a group consisting of oxy, amino, succinylamino, acetamido, aminopentanamido, aminoacetyl, thiopropanoayl, N-(mercaptomethyl)-propionamido, mercaptopropylthio)-propanoyl, (1,2-dihydroxy-3-mercaptopropylthio)-propanoyl, succinyl, acetyl, oxopentanoyl, carbamoyl, aminoalkyl, glutaramido, aminoethanethiol, mercaptopropanol, (hydroxypropylthio)-propanoayl, 3-((2-propionamidoethyl)-disulfanyl)propanoayl, (((acetamidoethyl)disulfanyl)-propanoyloxy)-glutaramido, aminoethanethioate, and 2-hydroxyacetic proprionic anhydride. More preferably $R_i$ has a molecular weight of less than about 650. Lipid may preferably be selected from diacylglycerols or a fatty acid the group consisting of oleate, myristate, linoleate and palmitate. The PEG chain may consist of between about 4 and 45 subunits. More preferably the PEG chain consists of between about 8 and 24 subunits. Still more preferably the PEG chain consists of between about 8 and 16 subunits.

In another aspect the invention includes a molecule comprising a compound represented by the following General Structure 15:

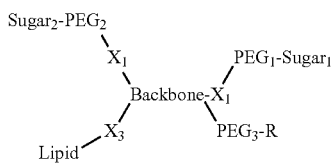

General Structure 15 where Sugar1 and Sugar2 may be the same or different carbohydrate selected from Table 6, the group consists of aldose, ketose, pyranose, furanose, trioses, tetroses, pentoses, hexoses, sucrose, lactose, maltose, trehalose, turanose, cellobiose, raffinose, melezitose, maltotriose, acarbose, stachyose; and where lipid is selected from alkyl groups (Tables 3 and 4) having between 4 and 22 carbons or bile acids having a particular steroid structure of 24 carbons (Table 5); and where $X_1$, $X_2$ and $X_3$ are the same or different linkers selected from Table 1 or 2 or a group consisting of one or more linkers selected from oxy, amino, succinylamino, acetamido, aminopentanamido, aminoacetyl, thiopropanoayl, N-(mercaptomethyl)propionamido, mercaptopropylthio)-propanoyl, (1,2-dihydroxy-3-mercaptopropylthio)propanoyl, succinyl, acetyl, oxopentanoyl, carbamoyl, aminoalkyl, glutaramido, aminoethanethiol, mercaptopropanol, (hydroxypropylthio) propanoayl, 3-((2-propionamidoethyl)disulfanyl)propanoayl, (((acetamidoethyl)disulfanyl)propanoyloxy)-glutaramido, aminoethanethioate, and 2-hydroxyacetic proprionic anhydride. More preferably $R_i$ has a molecular weight of less than about 650. R may be either —OH or —OCH₃. The lipid may preferably be selected from diacylglycerols or the group consisting of oleate, myristate, linoleate and palmitate. $PEG_1$, $PEG_2$ and $PEG_3$ may have the same or a different number of subunits. The PEG chain may consist of between about 3 and 45 subunits. More preferably the PEG chain consists of between about 3 and 24 subunits. Still more preferably the PEG chain consists of between about 4 and 16 subunits.

In another aspect the invention includes a molecule comprising a compound represented by the following General Structure 16:

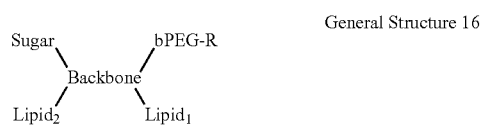

General Structure 16 where $Lipid_1$ and $Lipid_2$ may be the same or different alkyl groups diacylglycerols or carboxylic acids having between 4 and 22 carbons (Table 3 and 4) or bile acids having a particular steroid structure of 24 carbons (Table 5); where the backbone is selected from polyamine or compounds having four available binding sites; sugar is a carbohydrate including monosaccharides or disaccharides or oligosaccharides; where the four substitutable groups are covalently bond to the backbone through a etherification or esterification or amidification or similar substitution reactions. The General Structure is meant to include all racemers or structural isomers of the structure, as they can be functionally equivalent. Where the bPEG is a branched PEG with 2 or more PEG chains and each PEG chain may consist of between about 5 and 45 subunits. Where R is the terminal group and can be selected from a wide variety of chemical moieties. R preferably has a molecular weight of less than about 650. The PEG-carbohydrate-lipid conjugates are useful for applications other than liposomes, e.g., as a solvent.

Another aspect of the invention includes a method of delivering a compound, where the method comprises preparing a PEG-carbohydrate-lipid conjugate based formulation of the compound, where the formulation comprises a PEG-carbohydrate-lipid having an amino acid linker and possible secondary linker(s) selected from the group consisting of amino, succinylamino, acetamido, aminopentanamido, aminoacetyl, thiopropanoayl, N-(mercaptomethyl)propionamido, mercaptopropylthio)-propanoyl, (1,2-dihydroxy-3-mercaptopropylthio)propanoyl, succinyl, acetyl, oxopentanoyl, carbamoyl, aminoalkyl, glutaramido, aminoethanethiol, mercaptopropanol, (hydroxypropylthio)propanoayl, 3-((2-propionamidoethyl)disulfanyl)propanoayl, (((acetamidoethyl)disulfanyl) propanoyloxy)-glutaramido, aminoethanethioate, and 2-hydroxyacetic proprionic anhydride; and providing a release agent, where the release agent causes the linker to degrade. The release agent may be an acid, light, hypoxia, or a catalyst.

In one aspect, the invention is a method of linking the central backbone to any of the three carrier groups via an amino acid linkage. The carrier group may be activated by reacting it with disucccimidylcarbonate (DCS).

Example of the synthesis of the PEG-carbohydrate-lipid conjugates from amino acids is shown below in Reaction Scheme 1. The reaction scheme is applicable to carrier groups having all kinds of acyl or steroid acid groups.

Reaction Scheme 1

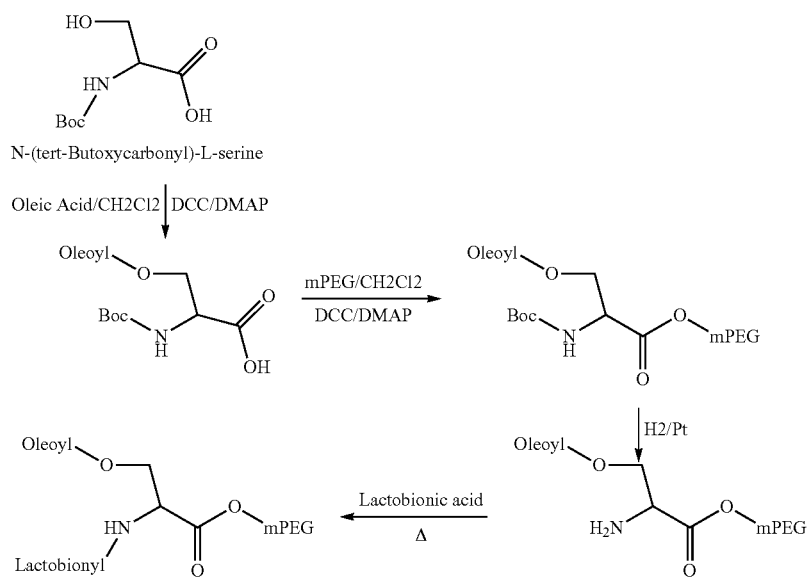

The activated acyl carrier group may then be directly reacted with an amino acid (AA) having a hydroxy group to produce a conjugate having an ester linkage. The carboxyl group of amino acid from AA-acylglycerate can react with one of hydroxy group of PEG and then the protection group on the primary amine is removed and reacted with the activated carbohydrate to form the PEG-lipid conjugates as depicted in Chemical Structure 3, where lipid may be a diacylglycerol or monoacyl group or fatty acid or steroid acid. The general structures shown in the application are meant to include all racemers and structural isomers of the structures, as they can be functionally equivalent.

Chemical Structure 3

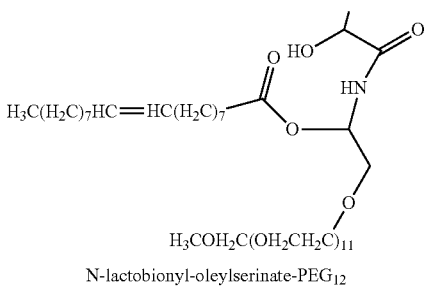

N-lactobionyl-oleylserinate-PEG$_{12}$

Example of the synthesis of the PEG-carbohydrate-lipid conjugates from glycerol or glycerol-like central backbones is shown below in Reaction Scheme 2. This reaction scheme is suitable for carrier groups with all kinds of acyl or steroid acid or PEG chains.

Reaction Scheme 2

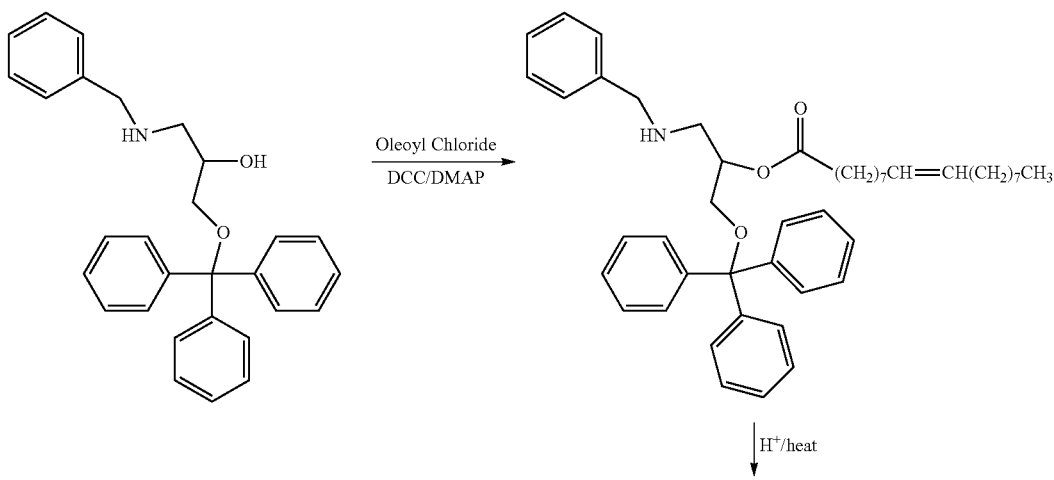

-continued
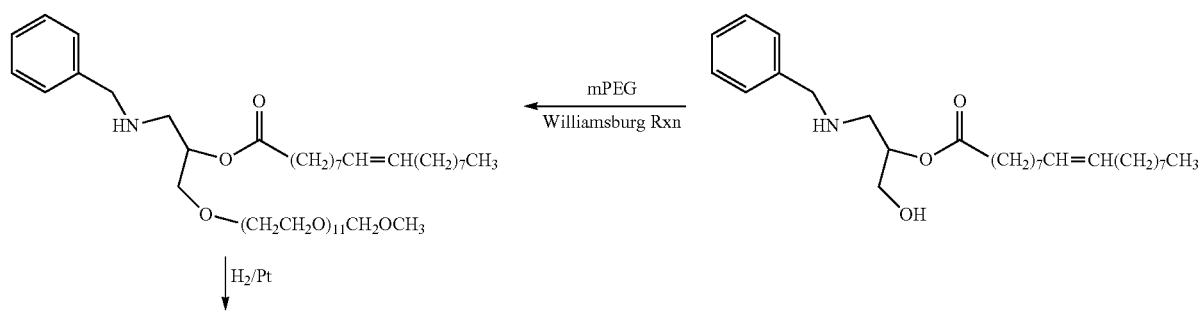
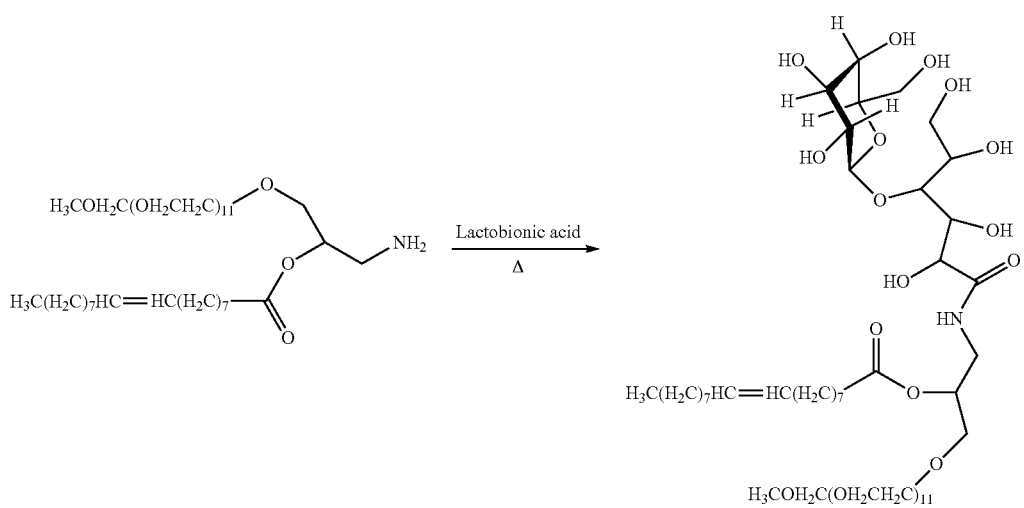
Reaction Scheme 3
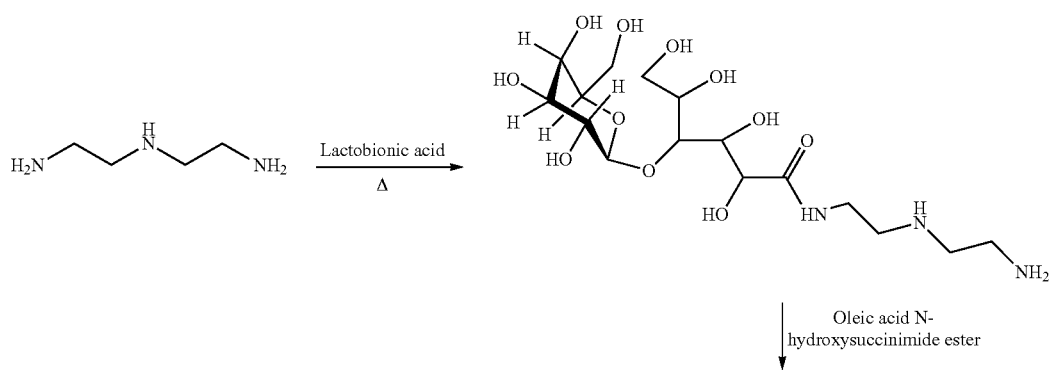

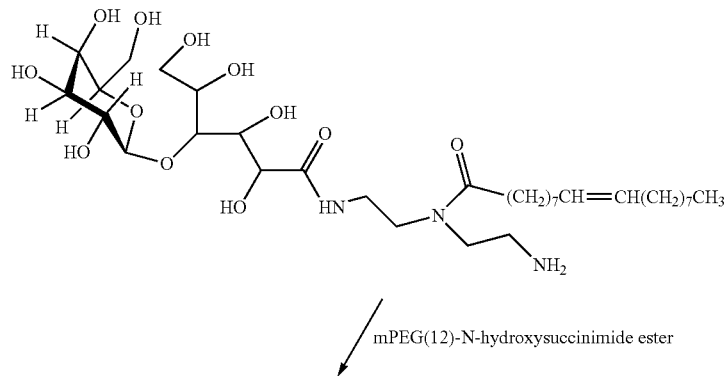

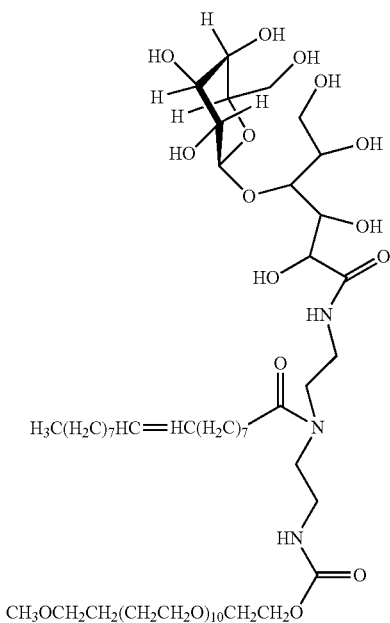

Example of the synthesis of the PEG-carbohydrate-lipid conjugates from linear multiamine central backbones is shown below in Reaction Scheme 3. Again, this reaction scheme is suitable for carrier groups with all kinds of acyl or steroid acid or PEG chains.

In another aspect, the invention includes Lipid-carbohydrate-PEG conjugates comprised of three carrier groups and a central backbone having at three positions available for the conjugation, and one or more linker(s) between one of the carrier groups and the central backbone. Such lipid-carbohydrate-PEG conjugates are represented by the Chemical Structures 1, where X may comprise a linker selected from Table 1 and 2 or a group consisting of amino, succinylamino, acetamido, aminopentanamido, aminoacetyl, thiopropanoayl, N-(mercaptomethyl)propionamido, mercaptopropylthio)-propanoyl, (1,2-dihydroxy-3-mercaptopropylthio)propanoyl, succinyl, acetyl, oxopentanoyl, carbamoyl, aminoalkyl, glutaramido, aminoethanethiol, mercaptopropanol, (hydroxypropylthio)-propanoayl, 3-((2-propionamidoethyl)disulfanyl)propanoayl, (((acetamidoethyl)disulfanyl)-propanoyloxy)glutaramido, aminoethanethioate, and 2-hydroxyacetic proprionic anhydride. The Table 7 shows certain samples of the PEG-Carbohydrate-Lipid Conjugates and in the event of variations of chemical names, the structures shown are meant to be controlling.

Sample structures of representative PEG-lipid conjugates are listed in Table 7.

TABLE 7
Sample of PEG-Carbohydrate-Lipid Conjugates
| Name | Chemical Structure |
|---|---|
| ODL-PEG: Oleoyldiethylenetriamine-PEG Lactobionate, n = 6 to 24 | 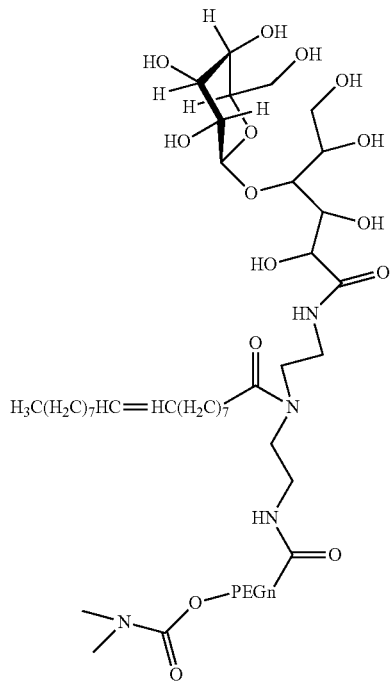 |
| ODL-bioPEG: Oleoyldiethylenetriamine-biotinylated PEG Lactobionate, n = 6 to 24 | 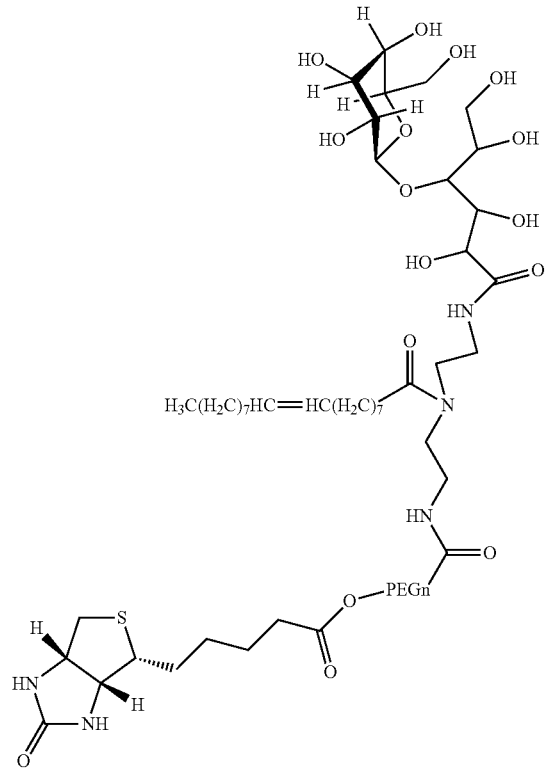 |

TABLE 7-continued
Sample of PEG-Carbohydrate-Lipid Conjugates
| Name | Chemical Structure |
|---|---|
| GDODL-12: Dioleoylglycerol-diethylenetriamine-monomethoxyl polyethylene glycol ether Lactobionate<br>n = 6 to 24 | 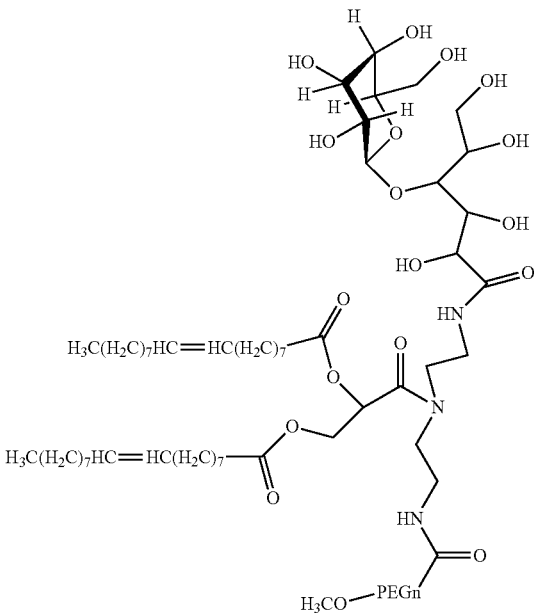 |
| OAPDL-PEG: oleoyl-N-(3-minopropyl)propane-1,3-diamine-monomethoxyl polyethylene glycol ether Lactobionate<br>n = 6 to 24 | 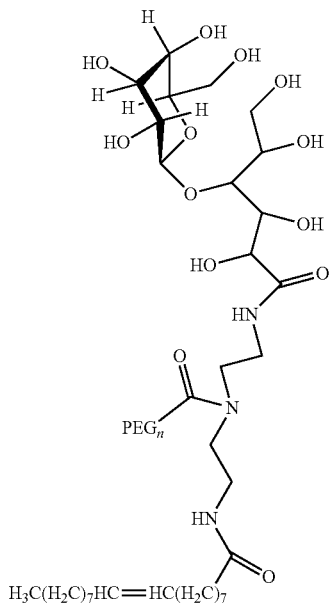 |

TABLE 7-continued
Sample of PEG-Carbohydrate-Lipid Conjugates
| Name | Chemical Structure |
| --- | --- |
| ODL-ThrPEG: Oleoyldiethylenetriamine-threoninyl PEG Lactobionate, n = 6 to 24 | 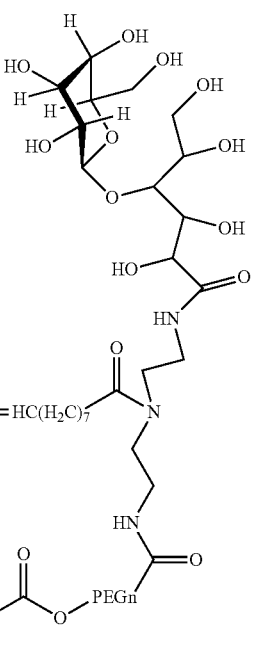 |
| ODL-TrpPEG: Oleoyldiethylenetriamine-Tryptophanyl PEG Lactobionate n = 6 to 24 | 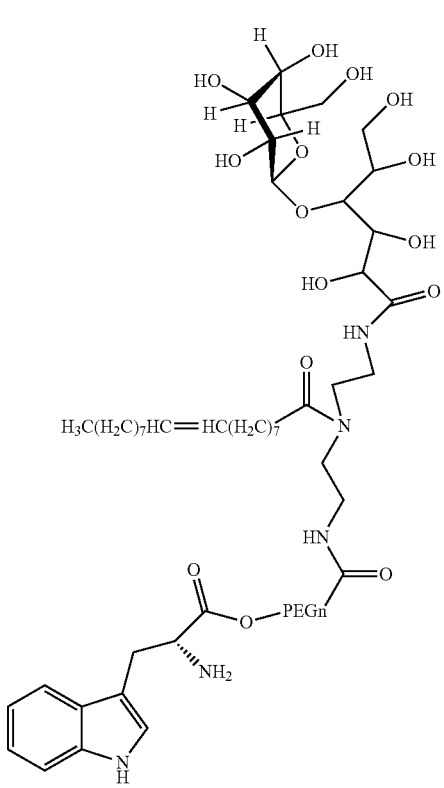 |

TABLE 7-continued
Sample of PEG-Carbohydrate-Lipid Conjugates
| Name | Chemical Structure |
|---|---|
| LOS-PEG: N- Lactobionyloleoyl-mPEG Serinate, n = 6 to 24 | 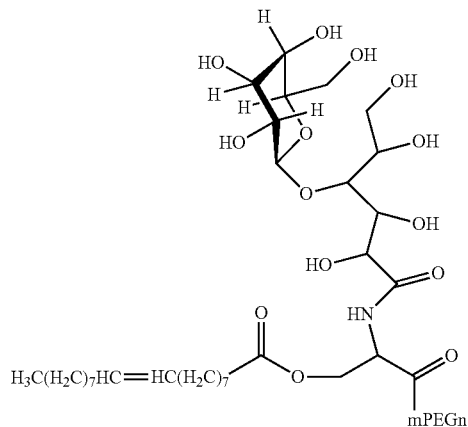 |
| OAPEL-PEG: Oleoyl(aminopropylamino)ethanoyl-mPEG Lactobionate n = 6 to 24 | 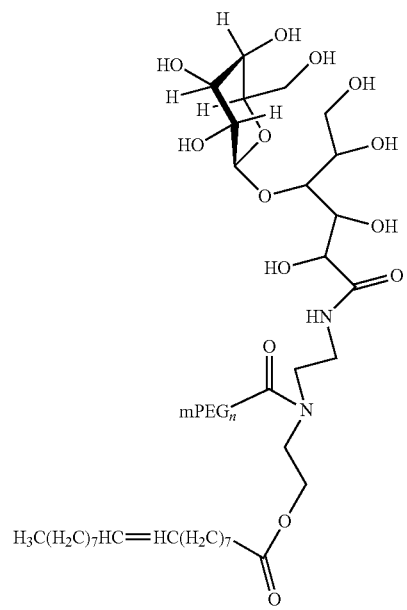 |

TABLE 7-continued
Sample of PEG-Carbohydrate-Lipid Conjugates
| Name | Chemical Structure |
|---|---|
| LOS-bioPEG: N- Lactobionyloleoyl-biotinylated PEG Serinate, n = 6 to 24 | 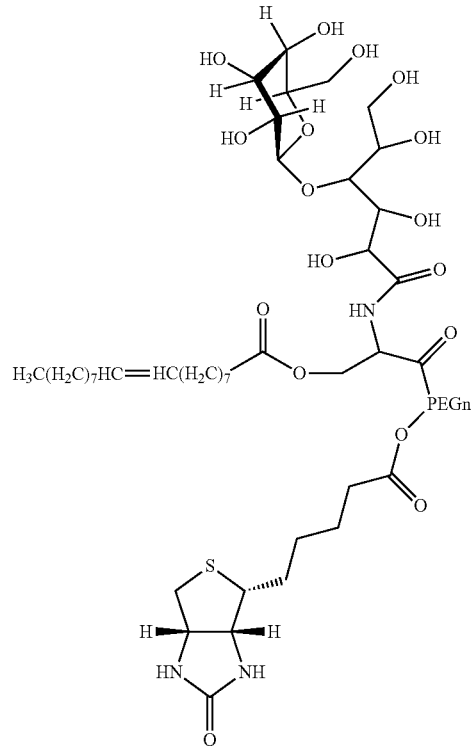 |
| DCAL-PEG: N- desoxycholylaspartate-mPEG Lactobionate, n = 6 to 24 | 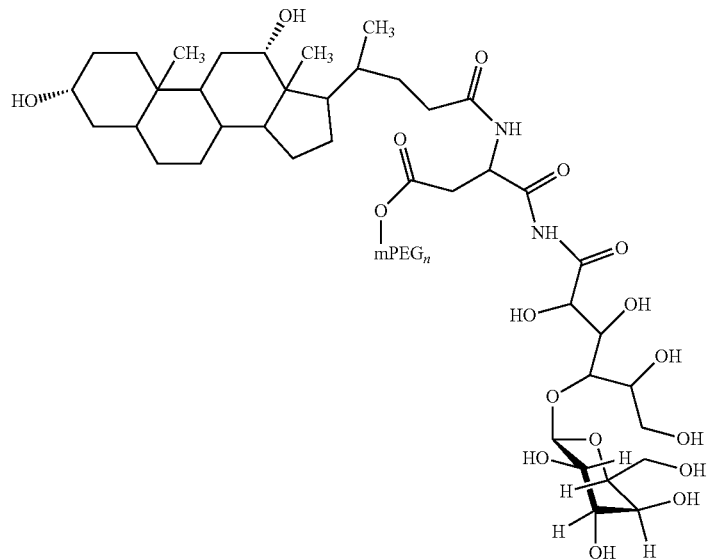 |

TABLE 7-continued

Sample of PEG-Carbohydrate-Lipid Conjugates

| Name | Chemical Structure |
|---|---|
| OAL-mPEG:<br>Oleoylaminopropanediol-mPEG Lactobionate, n = 6 to 24 | |
| OAL-bioPEG:<br>Oleoylaminopropanediol-biotinylated PEG Lactobionate, n = 6 to 24 | |
| DOTTL-PEG:<br>Dioeloyltriethylenetetramine-methoxylPEG Lactobionate<br>n = 8 to 24 | |

TABLE 7-continued
Sample of PEG-Carbohydrate-Lipid Conjugates
| Name | Chemical Structure |
|---|---|
| DLTTO-mPEG: Dilactobionyltriethylenetetramine-oleate-monomethoxyl PEG ether n = 8 to 24 | 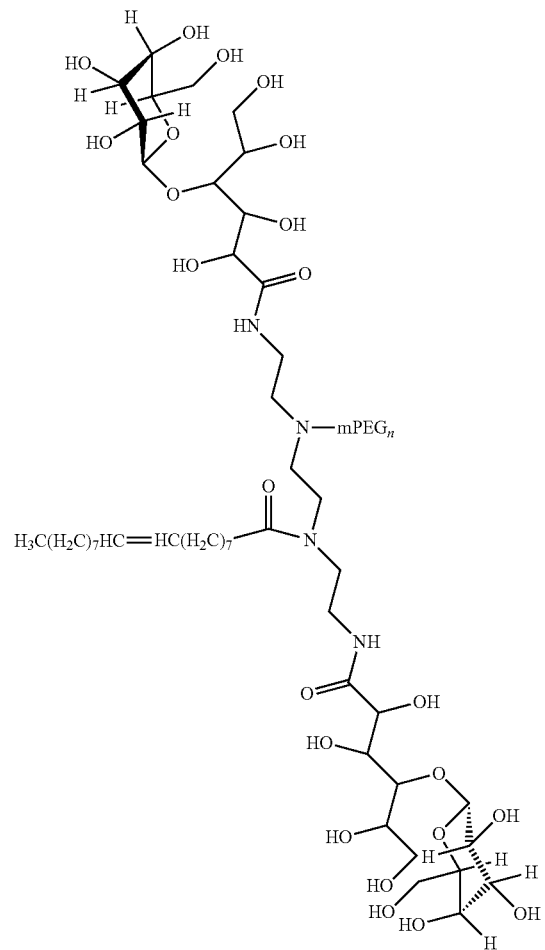 |

TABLE 7-continued

Sample of PEG-Carbohydrate-Lipid Conjugates

| Name | Chemical Structure |
| --- | --- |
| DOL-bPEG: Dioleoyl-branched methoxyl PEG ether Lactobionate<br>n = 8 to 24 | 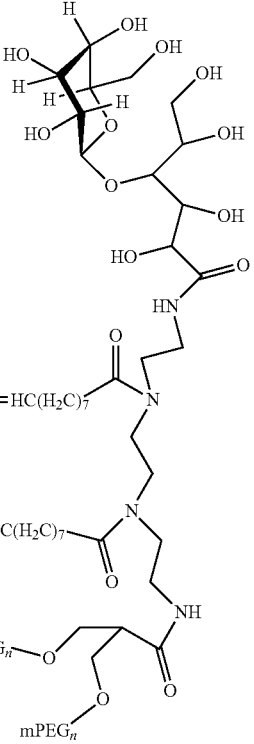 |

Embodiments of the present invention are described herein in the context of preparation of pharmaceutical compositions including purified PEG-lipid conjugates for increasing the solubility and enhancing the delivery of active agents. The approximate preferable compositions for formulated drug products are generally described herein, though different drugs typically have differing optimal formulations.

For IV solutions, the preferable concentration of drug is 0.1% to 30%. More preferable is 0.5 to 10%. Most preferable is 0.5 to 5%. The preferable weight ratio of PEG-lipid to the drug (PEG-Lipid/drug) in the final drug solution for the injection is 1 to 30. More preferable is 1 to 20. Most preferable is 1 to 10.

It is preferable PEG-carbohydrate-lipid conjugates having monodisperse PEG chains for intravenous administration of pharmaceutical agents. The monodisperse PEG chains may consist of one or more PEG oligomers where the total oligomer purity from individual oligomers should be higher than 90%. For instance, a monodisperse PEG chain may contain 50% of PEG-12 and 40% of PEG-15. It is preferable to have a monodisperse PEG chain containing a few numbers of oligomers. The preferable number of oligomer is 1 to 5, more preferable is 1 to 3. Most preferable is 1 to 2.

For oral solutions, the preferable concentration of drug is 1% to 40%. More preferable is 2.5 to 30%. Most preferable is 5 to 30%. The preferable ratio of PEG-lipid to the drug (PEG-Lipid/drug) is 0.5 to 20. More preferable is 1 to 10. Most preferable is 1 to 5.

For ophthalmic preparations, the preferable concentration of drug is 0.01 to 5%. More preferable is 0.05 to 2%. Most preferable is 0.1 to 2%. The preferable ratio of PEG-lipid to the drug (PEG-Lipid/drug) is 1 to 20. More preferable is 3 to 15. Most preferable is 5 to 10.

For topical solutions, the preferable concentration of drug is 0.05 to 5%. More preferable is 0.1 to 5%. Most preferable is 0.1 to 2%. The preferable ratio of PEG-lipid to the drug (PEG-Lipid/drug) is 1 to 20. More preferable is 3 to 15. Most preferable is 5 to 10.

For oral capsules, the preferable capsule content of drug is 10 mg to 250 mg. More preferable is 25 mg to 200 mg. Most preferable is 25 mg to 100 mg. The preferable ratio of PEG-lipid to the drug (PEG-Lipid/drug) is 1 to 10. More preferable is 1 to 5. Most preferable is 2 to 5.

For topical preparations, the preferable concentration of active is 0.5 to 5%, more preferable is 0.5 to 2%, most preferable is 1 to 2%. The preferable ratio of PEG-lipid to the drug (PEG-Lipid/drug) is 1 to 30, more preferable is 1 to 20, most preferable is 3 to 10.

While the foregoing discussion has focused on polymer-carbohydrate-lipid conjugates having a glycerol-like backbone including a PEG chain, the invention further includes alternate backbones and polymers. 3-amino-1,2-propanediol, 3-bromo-1,2-propanediol, 3-chloro-1,2-propanediol, 3-fluoro-1,2-propanediol, DL-glyceric acid, dimethylol propionic acid (2,2-bis(hydroxymethyl)propionic acid), tartaric acid, glucoheptonic acid and 1,2,4-butanetriol may be used as alternative backbones to synthesize similar PEG-carbohydrate-lipid conjugates. In such alternative embodiments, the PEG chain (or alternative polymer chain) is preferable as monodisperse or narrow dispersive, especially for intravenous administration of pharmaceutical products.

In another aspect, the polymer-sugar-lipid conjugates having a amino acid central component or backbone including a PEG chain, the invention further includes those amino acids with two carboxyl groups or two hydroxyl or two amino groups. Preferable amino acids are Aspartic Acid, Glutamic Acid, Glutamine, Asparagine, Serine, Threonine, Arginine, Histidine, Lysine, Ornithine, Threonine, Tryptophan and Tyrosine, more preferable are Aspartic Acid, Glutamic Acid, Ornithine, Serine and Threonine, and most preferable are Aspartic Acid, Glutamic Acid, Ornithine and Serine. In lipid-amino acid-sugar-PEG conjugates, the PEG chain (or alternative polymer chain) is preferable as monodisperse or narrow dispersive, specifically for intravenous administration of pharmaceutical products.

In another aspect, the polymer-lipid conjugates having a linear multiamine central component or backbone including a PEG chains, the invention further includes those linear amines are suitable to be used as the central backbones including and not limited to diethylenetriamine (spermidine), triethylenetriamine (spermine), norspermidine, bis(3-aminopropyl)-1,3-propanediamine, bis(hexamethylene)triamine. In lipid-linear multiamine-sugar-PEG conjugates, the PEG chain (or alternative polymer chain) is preferable as monodisperse narrow dispersive, specifically for intravenous administration of pharmaceutical products.

EXAMPLES

Chemicals and Reagents: N,N'-dicyclohexylurea, N,N'-dicyclohexylcarbodiimide, lactobionic acid, and other chemicals were obtained from Sigma-Aldrich (St. Louis, Mo., USA). Activated PEG or biotinylated PEG were obtained from Quanta BioDesign (Powell, Ohio, USA) or Thermo Fisher Scientific (Rockford, Ill.).

Example 1

Preparation of tert-Butyl Carbamates (Boc)-Protected Amino Groups

A high yield and effective synthetic method under a catalyst-free and room temperature was reported previously [Chankeshwara, S V and Chakraborti, A K. *Org. Lett.,* 2006; 8, 3259] and used with slightly modification. To a solution of starting compound containing amino group in MeOH, di-t-butyl dicarbonate was added as one to one molar ratio. The resulting mixture was stirred overnight at room temperature. When the reaction was done, solvent was removed under Vacuum, the residue was dissolved into EtOAc and washed with saturated $NH_4Cl$ aqueous solution once, then dried over $Na_2SO_4$ and condensed to yield the expected product (>90%). Example of this reaction is demonstrated in Reaction Scheme 4. This method gives N-t-Boc derivatives chemoselectively without any side products (such as isocyanate, urea, N,N-di-t-Boc).

Reaction Scheme 4

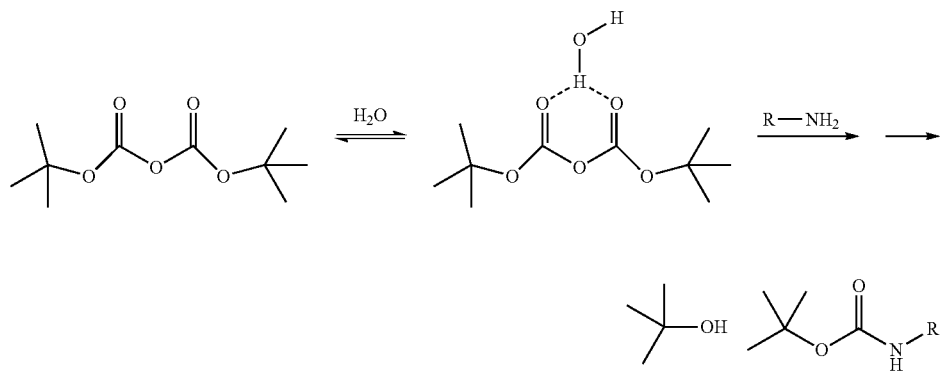

Example 2

Deprotection of Boc-Protected Amino Groups

Effective reagents for the deprotection of tert-butyl carbamates or tert-butyl esters include phosphoric acid and trifluoroacetic acid. The reactions give high yields and very convenient [Li, B. Berliner, M. etc, *J. Org. Chem.,* 2006; 71, 9045]. Equal volumes of Trifluoroacetic acid was added to a solution of Boc-carbamate (10% of crude product) in $CH_2Cl_2$. The resulting solution was stirred at room temperature for overnight and the solvent was evaporated and the residue was re-dissolved into $CH_2Cl_2$, then washed with saturated $NaHCO_3$ and dried over $MgSO_4$. Solvent was evaporated and was used in next step without further purification.

Example 3

Preparation of Oleoyl Serinate 0.03 moles of N-Boc-serine was constantly stirred under nitrogen in 100 mL of chloroform. 0.03 mole of oleoyl chloride was dissolved with 100 mL of chloroform and added to this heterogeneous mixture of N-Oleoylserine and followed by adding 10 mL of anhydrous pyridine. The reaction for 30 minutes under constantly stirring at room temperature, the mixture turned to homogeneous and the reaction was completed when no detectable oleoyl chloride was in the mixture. The bulk solvent was removed under vacuum and the crude product was used to next step without further purification. The resulting product (% of yields 75-80) is showed in Chemical Structure 4.

Chemical Structure 4

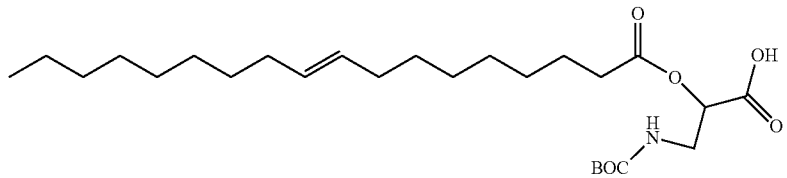

Example 4

Preparation of oleoyl-dodecaethylene glycol serinate 0.01 moles of mono methoxyl dodecaethylene glycol ether (0.01 mmol) was dissolved with 50 mL of anhydrous $CH_2Cl_2$, 0.01 moles of dicyclohexylcarbodiimide and dioleoylserine were added. The resulting mixture was stirred at 0° C. for 2 hours, then allowed to warm up to room temperature and stirred for additional 48 hours. When the reaction was complete, the white precipitate was filtered off over celite. The residue was rinsed with small amount of $CH_2Cl_2$ twice and washed with sutured $NH_4Cl$, then dried over $MgSO_4$. Solvent was evaporated to afford pale yellowish oil as showed in Chemical Structure 5. The crude product's purity was determined by $^1H$ NMR and UPLC-MS, ESI-MS (>80%).

Chemical Structure 5

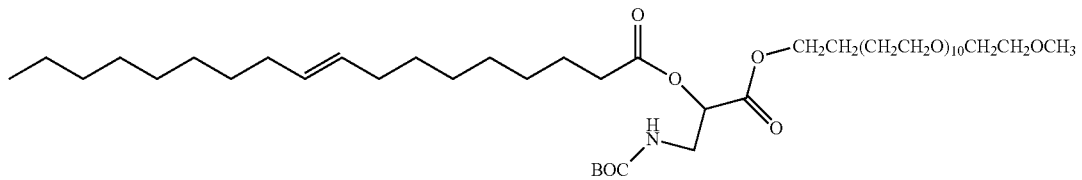

Example 5

Preparation of oleoylserinylmonomethoxyldodecaethylene glycol lactobionate

The protection group of tert-butyl carbamate on the amino group was removed according to the method described in Example 2. 0.01 moles of oleoylserinylmonomethoxyl-dodecaethylene glycol (0.01 mmol) from Example 4 was dissolved with 50 mL of anhydrous N-methyl-2-pyrrolidinone, 0.01 moles of Lactobionolactone was added. The resulting mixture was stirred at 50-60° C. for overnight, and allowed to cool to the room temperature. The reaction solution was precipitated into isopropyl alcohol (IPA) and methyl t-butyl ether (MTBE) was added to maximize the isolated yield of precipitate. The crude product was washed well with 50/50 (v/v) IPA/MTBE and dried under vacuum at 30-40° C. The purity (>95%) of the final product (Chemical Structure 6) was determined by $^1H$ NMR and UPLC-MS.

Chemical Structure 6

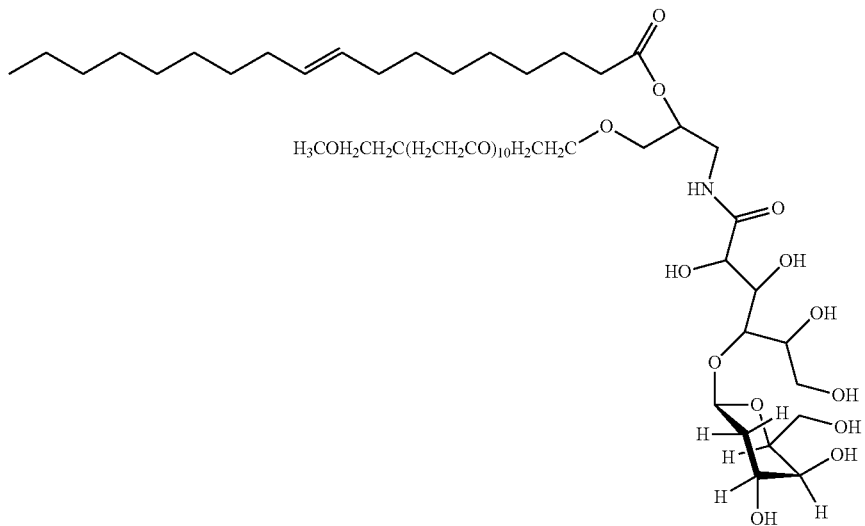

Example 6

Preparation of lactobionyldiethylenetriamine

Diethylenetriamine (0.01 mol) was dissolved in 50 mL of dry (molecular sieve) N-methyl-2-pyrrolidinone and lactobionolactone (0.005 mol) was added. The resulting mixture was stirred for 6 hours at 50-60° C. and allowed to cool to the room temperature when the reaction was completed. The reaction solution was precipitated into isopropyl alcohol (IPA) and methyl t-butyl ether (MTBE) was added to maximize the isolated yield of precipitate. The cake was washed well with 50/50 (v/v) IPA/MTBE and dried under vacuum at 30-40° C. The crude product (Chemical Structure 7) and was used in next step without further purification.

Chemical Structure 7

Example 7

Preparation of Lactobionyloleoyldiethylenetriamine-mPEG 0.01 mole of the starting material from Example 6, lactobionyldiethylenetriamine, was dissolved in 20 mL of dimethylformamide (DMF) at 20 to 30° C. The slightly excess active oleic acid N-hydroxysuccinimide ester (0.011 mol) was dissolved in 20 mL of tetrahydrofuran (THF), then mixed with lactobionyldiethylenetriamine and adding triethylamine (TEA, 3%, v/v) as a base, stirred for 2 hrs at room temperature. An assay was performed to verify the yield and moves to next the step 2 without purification. The active mPEG$_{24}$-NHS (0.01 mol) was dissolved in DMF, then mixed with the above reactants, stirred for overnight at room temperature. After the completion of the reaction, solvents were removed by vacuo and 50 mL of acetone was added to the crude product and filtered and washed with 30 mL of acetone three times. The wet product (60-70%) was further lyophilized to a wax as showed in Chemical Structure 8.

Chemical structure 8

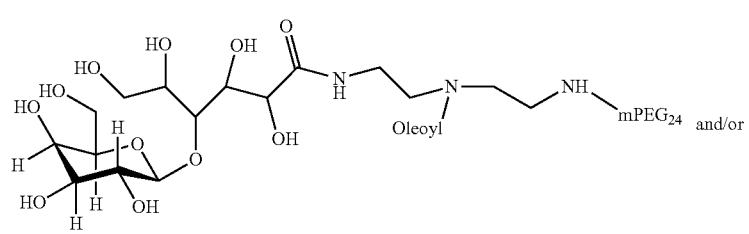

-continued

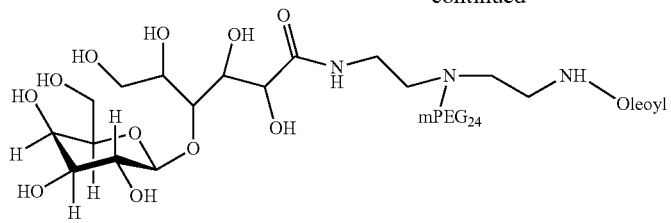

Example 8

Preparation of lactobionyltrethylenetetramine

Triethylenetetramine (0.01 mol) was dissolved in 50 mL of dry (molecular sieve) N,N-Dimethylformamide (DMF) and lactobionic acid (0.01 mol) was added. The resulting mixture was stirred for 6 hours at 50-60° C. and allowed to cool to the room temperature when the reaction was completed. The reaction solution was precipitated into isopropyl alcohol (IPA) and methyl t-butyl ether (MTBE) was added to maximize the isolated yield of precipitate. The cake was washed well with acetone, then 50/50 (v/v) IPA/MTBE and dried under vacuum at 30-40° C. The crude product (Chemical Structure 9) and was used in next step without further purification.

Chemical Structure 9

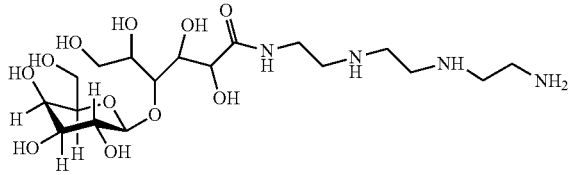

Example 9

Preparation of Lactobionyloleoyltriethylenetetramine-mPEG 0.01 mole of the starting material from Example 2, lactobionyltriethylenetetramine, was dissolved in 20 mL of dimethylformamide (DMF) at 20 to 30° C., the active mPEG$_{24}$-NHS (0.01 mol in 10 mL DMF) was added, stirred for 2 hrs at room temperature. An assay was performed to verify the yield and moves to the next step without purification. The slightly excess active N-hydroxysuccinimide ester of oleic acid (0.021 mol) was dissolved in 40 mL of DMF, then mixed with above reactants and adding triethylamine (TEA, 3%, v/v) as a base, stirred for overnight at room temperature. 300 mL of acetone was added at the end of the reaction and solvents were removed by vacuo. The crude product washed with acetone and filtered. The wet product (55-70%) was further lyophilized to a wax as showed in Chemical Structure 10.

Chemical Structure 10

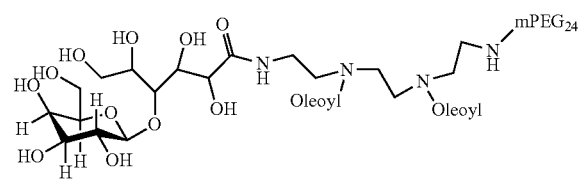

Similar synthetic methods from the Examples 1 to 9 can be utilized for the preparations of other PEG-carbohydrate-lipid conjugates, some of these PEG-carbohydrate-lipid conjugates are shown in Table 7.

In another aspect, the polymer chain can be replaced by other polymer(s) such as polymethylene glycol or polypropylene glycol or a mixture of the repeating units of methylene glycol, ethylene glycol and propylene glycol. Hydrophilic polymers useful in forming the polymer-lipid conjugates of the invention include polyethyleneglycol (PEG) and other polyalkene oxide polymers, polyoxyethylene alkyl ethers, polyvinylpyrrolidone, Poly(Allyl Amine), Poly(1-glycerol methacrylate), Poly(2-ethyl-2-oxazoline), Poly(2-hydroxyethyl methacrylate/methacrylic acid)/poly(2-hydroxyethyl methacrylate), Poly(2-vinylpyridine), Poly(acrylamide/acrylic acid), Poly(acrylic acid), Poly(butadiene/maleic acid), Poly(ethyl acrylate/acrylic acid), Poly(ethylene oxide-b-propylene oxide), Poly(ethylene/acrylic acid), Poly(methacrylic acid), Poly(maleic acid), Poly(N-iso-propylacrylamide), Poly(N-vinylpyrrolidone/vinyl acetate), Poly(styrenesulfonic acid), Poly(styrenesulfonic acid/maleic acid), Poly(vinyl acetate), Poly(vinyl phosphoric acid), Poly(vinylamine), Polyacrylamide, Polyacrylic Acid, Polyaniline, Polyethylenimine, Pullulan, Polymethacrylamide. Copolymers and block copolymers based on the list above may also be used. The free polymers are water-soluble at room temperature, as well as non-toxic. They do not elicit an appreciable immunogenic response in mammals. Hydrophilic polymers with narrow molecular weight distributions are preferable. Because of already existing acceptance in the pharmaceutical business, PEG is the preferred hydrophilic polymer.

Example 9

Oral Solution Compositions

PEG-lipid was added to a vessel equipped with a mixer propeller. The drug substance was added with constant mixing. Mixing continued until the drug was visually dispersed in the lipids. Pre-dissolved excipients were slowly added to the vessel with adequate mixing. Mixing continued until fully a homogenous solution was achieved. A sample formulation is described in Table 8.

TABLE 8

| Ingredient | mg/mL |
| --- | --- |
| Drug Substance (active) | 30.0 |
| Liquid PEG-carbohydrate-lipid | 150 |
| Sodium Hydroxide | See below |
| Hydrochloric Acid | See below |
| Sodium Benzoate | 2.0 |
| Artificial Flavor | 5.0 |
| Purified Water | qs 1 mL |

The liquid lipid may be any of PEG-carbohydrate-lipid conjugates with a shorter PEG chain consisting of between about 6 and 16 subunits. Sodium hydroxide is used to prepare a 10% w/w solution in purified water. The targeted pH is in a range of 4.0 to 7.0. NaOH is used to adjust pH if necessary. The drug may be modafinil or nifedapine or esomeprazole or rapamycin or a fungicide or another active agent.

Example 10

Injection Solution Compositions

All product contact equipment must be clean and sanitized. PEG-lipid was added to a vessel equipped with a mixer propeller. The drug substance was added with constant mixing. Mixing continued until the drug was visually dispersed in the lipids. Pre-dissolved excipients were slowly added to the vessel with adequate mixing. Mixing continued until fully a homogenous solution was achieved. Stainless steel cover for premix vessel to help maintain nitrogen overlay, at least two jacketed, pressurizable, stainless steel tanks equipped with agitation and capable of nitrogen overlay were needed. The mixture in the tank with a nitrogen overlay and agitation was held for 1 hour to reduce dissolved oxygen content in the product. The tank impeller mixing speed was approximately 45-50 RPM and compressed air supply pressure to the mixer was between 10-13 psig. Mixing rates can be adjusted as required to prevent foaming of product. Using aseptic technique, a 5 mL sample as taken for pH measurement. If necessary, 1.0 N Sodium Hydroxide solution or 20% Phosphoric Acid solution was used to adjust the pH of the product to 6.0-8.0. Filled the product in a sterile-filtered nitrogen environment into washed and sterilized 5-mL Type 1 glass vials and each vial was sealed with a sterilized 13-mm pharma grade rubber solution stopper and crimped with a sanitized 13-mm pharma grade flip-off aluminum seal. A sample formulation is described in Table 9.

TABLE 9

| Ingredient | mg/mL |
| --- | --- |
| Drug Substance (Active) | 30.0 |
| PEG-carbohydrate-lipid | 150 |
| Sodium Phosphate, Monobasic, Monohydrate, Crystal | 0.040 |
| Sodium Hydroxide | for pH adjustment |
| Phosphoric Acid | for pH adjustment |
| Water for Injection | qs 1.0 mL |

The liquid lipid may be any of PEG-carbohydrate-lipid conjugates with a shorter PEG chain consisting of between about 6 and 16 subunits. Sodium hydroxide is used to prepare a 10% w/w solution in purified water. The targeted pH is in a range of 6.0 to 8.0. NaOH or phosphoric acid is used to adjust pH if necessary. The drug may be modafinil or nifedapine or esomeprazole or rapamycin or fungicide or anticancer agent of tinib or another active agent.

Example 11

Topical Cream Composition

PEG-carbohydrate-lipid was added to a stainless steel vessel equipped with propeller type mixing blades. The drug substance was added with constant mixing. Mixing continued until the drug was visually dispersed in the lipids at a temperature to 60°-65° C. Organic acid, Cholesterol and glycerin were added with mixing. Ethanol and ethyoxydiglycol were added with mixing. Finally Carbopol ETD 2020, purified water and triethylamine were added with mixing. Mixing continued until fully a homogenous cream was achieved. The formulation is described in Table 10.

TABLE 10

| Ingredient | % |
| --- | --- |
| Drug Substance (Active) | 1.0 |
| PEG-carbohydrate-lipid | 5.0 |
| Carbopol ETD 2020 | 0.5 |
| Ethyoxydiglycol | 1.0 |
| Ethanol | 5.0 |
| Glycerin | 1.0 |
| Cholesterol | 0.4 |
| Triethylamine | 0.20 |
| Organic acid | 10 |
| Sodium hydroxide | See below |
| Purified water | qs 100 |

The lipid may be any of PEG-carbohydrate-lipid conjugates with a PEG chain consisting of between about 6 and 24 subunits. Organic acid may be lactic acid or pyruvic acid or glycolic acid. Sodium hydroxide is used to adjust pH if necessary. The targeted pH range was between 3.5 and 7.0. The drug may be itraconazole, posaconazole, voriconazole or equaconazole, Terbinafine, Amorolfine, Naftifine, Butenafine, Benzoic acid, Ciclopirox, Tolnaftate, Undecylenic acid, Flucytosine, Griseofulvin, Haloprogin, Sodium bicarbonate or Fluocinolone acetonide or azithromycin.

Example 12

Topical Solution Composition

The topical solution was prepared as in Example 11, a sample formulation is described in Table 11.

TABLE 11

| Ingredient | % |
| --- | --- |
| Drug Substance (Active) | 1.0 |
| PEG Lipid | 5.0 |
| α-Tocopherol | 0.5 |
| Organic acid | 10.0 |
| Ethanol | 5.0 |
| Sodium Benzoate | 0.2 |
| Sodium Hydroxide | See Below |
| Purified Water | qs 100 |

The lipid may be any of PEG-carbohydrate-lipid conjugates with a PEG chain consisting of between about 6 and 16 subunits. Organic acid may be lactic acid or pyruvic acid or glycolic acid. Sodium hydroxide is used to adjust pH if necessary. The targeted pH range was between 3.5 and 7.0. The drug may be itraconazole, posaconazole, voriconazole or equaconazole, Terbinafine, Amorolfine, Naftifine, Butenafine, Benzoic acid, Ciclopirox, Tolnaftate, Undecylenic acid, Flucytosine, Griseofulvin, Haloprogin, Sodium bicarbonate or Fluocinolone acetonide or azithromycin.

Example 13

Anti-Infective Ophthalmic Compositions

PEG-carbohydrate-lipid was added to a vessel equipped with a mixer propeller. The azithromycin drug substance was added with constant mixing. Mixing continued until the drug was visually dispersed in the lipids. Pre-dissolved excipients and sterile purified water were slowly added to the vessel with adequate mixing. Mixing continued until fully a homogenous solution was achieved. A sample formulation is described in Table 12.

TABLE 12

| Ingredient | mg/mL |
|---|---|
| Active | 15 mg |
| PEG Lipid | 150 |
| Sodium Hydroxide | See below |
| Hydrochloric Acid | See below |
| Sodium Chloride | 9 |
| Sterile purified water | qs 1 mL |

The lipid may be any of PEG-carbohydrate-lipid conjugates with a PEG chain consisting of between about 6 and 16 subunits. Sodium hydroxide is used to prepare a 10% w/w solution in purified water. The targeted pH is in a range of 7.0 to 7.8. NaOH is used to adjust pH if necessary. The active may be azithromycin or itraconazole or posaconazole or voriconazole or another active agent.

Example 14

Stability of Peptide Solution

Stability experiment was carried out by HPLC assay and a custom synthesized thermolabile peptide with the following sequence was used as the model compound: Phe-Pro-Lys-Leu-Ser-His-Gly-Cys-Asn-Lys-His-Ser-Arg-Lys-His-Pro-Tyr-Met-Thr-Phe. The peptide was added to selected media and sonicated for 10 minutes. The sample solutions were filtered through passed through 0.22-μm pore-size filter to remove dust particles before the HPLC assay. A Simadzu 10avp chromatography system with a Kinetex $C_{18}$ (2.6 μm, 100×4.6 mm i.d.) column (Phenomenex, Torrance, Calif.) were used. The solutions were kept at 25° C. in the Autosampler during the assay and the mobile phase consisted of 0.1% of trifluoroacetic acid and acetonitrile mixture (v/v, 80/20) with a flow rate of 1.0 mL/min. The peptide peak was monitored at 210 nm and quantitated using external standard sets of the peptide. The assay results are summarized in Table 13. As showed in the FIG. 1, the peptide was degraded significantly in 24 hours in a 50 mM of phosphate buffer, in the contrast; more than 97% of the peptide was still remaining in a 2% of PEG-carbohydrate-lipid after the same period of the time.

TABLE 13

Peptide Stability Study
Peptide Assay

| Time | Buffer (pH 7.0)[1] | | ODL-15 (pH 7.0)[2] | | ODL-15 (pH 8.0)[3] | |
|---|---|---|---|---|---|---|
| (hr) | Peak area | % | Peak area | % | Peak area | % |
| 0 | 650000 | 100.0 | 650000 | 100.0 | 650000 | 100.0 |
| 2 | 612300 | 94.2 | 651300 | 100.2 | 636350 | 97.9 |
| 4 | 568750 | 87.5 | 649350 | 99.9 | 624650 | 96.1 |
| 6 | 564850 | 86.9 | 642850 | 98.9 | 622050 | 95.7 |
| 8 | 557050 | 85.7 | 640900 | 98.6 | 615550 | 94.7 |
| 9 | 546650 | 84.1 | 640250 | 98.5 | 612300 | 94.2 |
| 10 | 535600 | 82.4 | 638950 | 98.3 | 609050 | 93.7 |
| 12 | 520650 | 80.1 | 637650 | 98.1 | 604500 | 93.0 |
| 18 | 495950 | 76.3 | 637000 | 98.0 | 592800 | 91.2 |
| 24 | 484250 | 74.5 | 634400 | 97.6 | 583050 | 89.7 |

Figure 2:
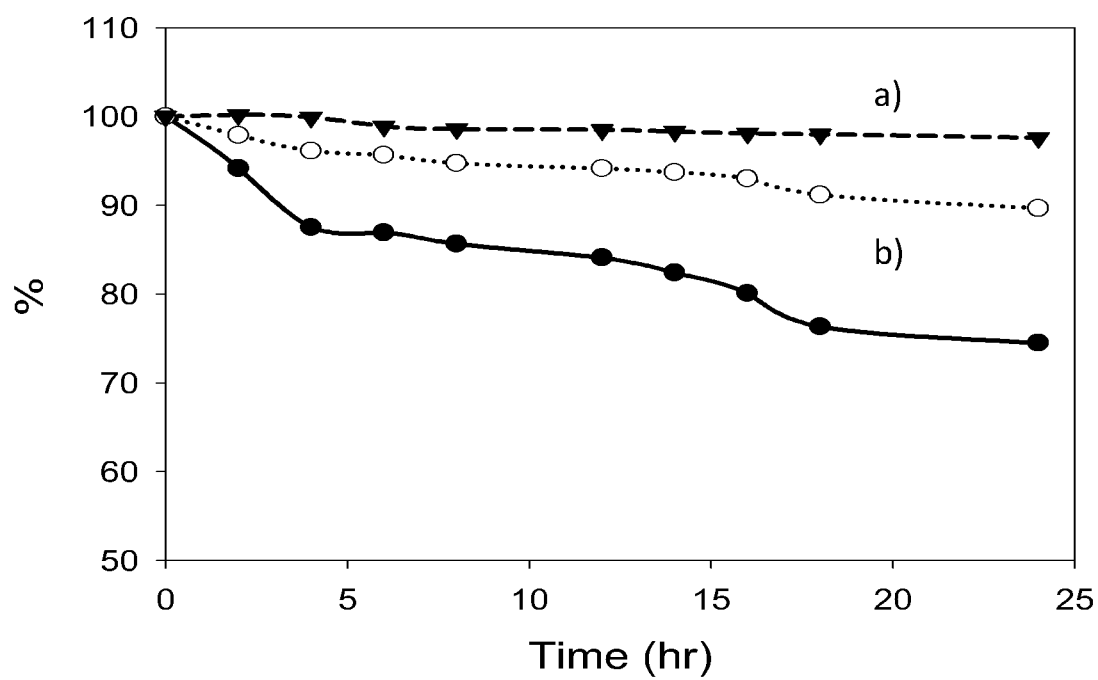
FIG. 2 shows stability profiles of a sample peptide in a) 2% ODL-15 in 50 mM sodium phosphate buffer (pH 7.0), b) 2% ODL-15 in 50 mM sodium phosphate buffer (pH 8.0) and c) 50 mM sodium phosphate buffer (pH 7.0). The plots were the % recovery vs. time.

[1]50 mM of sodium phosphate buffer
[2]Same as 1 and 2% of ODL-15 (ODL-PEG$_{15}$) was added
[3]Same as 2 and the pH was adjusted with 1N of NaOH FIG. 2 shows the peptide stability profile of 100 μg peptide/mL in a) 2% ODL-PEG$_{15}$ in 50 mM sodium phosphate buffer (pH 7.0), b) 2% ODL-PEG$_{15}$ in 50 mM sodium phosphate buffer (pH 8.0) and c) 50 mM sodium phosphate buffer (pH 7.0). The plots were the % recovery vs. time.

Example 15

Pharmacokinetic Profile of Lapatinib Formulations

Experiments were performed to determine blood levels of Lapatinib formulations after intravenous injections. For comparison, Lapatinib formulated in Cremophor® were also tested. Groups of three male mice (B6D2F1) were used for the studies. HPLC-MS analyses were performed on heparinized mouse plasma samples obtained typically at 0.17 hr, 0.5 hr, 1 hr, 2 hr, 4 hr, 12 and 24 hr after bolus IV injections. To determine the level of the drug, acetonitrile were first used to extract the compound and to remove proteins in samples. An isocratic HPLC-MS/MS method was then used to separate the drugs from any potential interference. Drug levels were measured by MS detection with a multiple reaction monitoring (MRM) mode. PK data was analyzed using the WinNonlin program (ver. 5.3, Pharsight) non compartmental model of analysis. The results demonstrated that formulations of compound(s) in the present invention have a superior PK profile than in Cremophor EL®.

Figure 3:
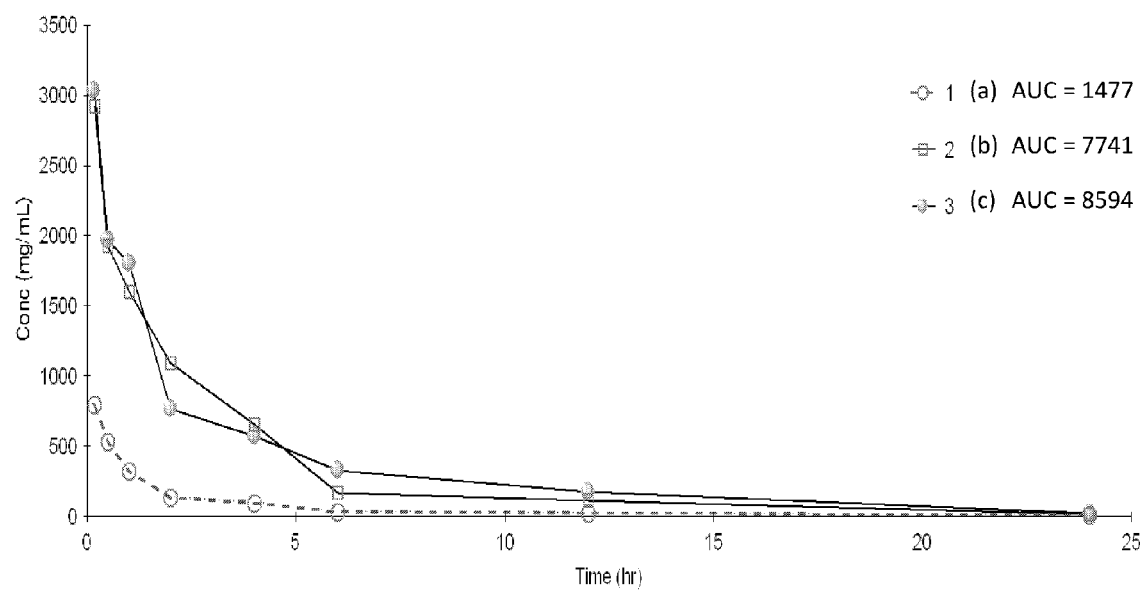
FIG. 3 shows Lapatinib mouse PK profiles of (a) 5% Cremophor EL® plus 5% methanol in 10 mM sodium phosphate buffer (pH 7.0), b) 1% ODL-15 in 10 mM sodium phosphate buffer (pH 7.0), (b) 2% ODL-15 in 10 mM sodium phosphate buffer (pH 7.0) and the drug was administered intravenously and the dosing strength was 10 mg/kg.

FIG. 3 shows Laptinib mouse PK profiles of (a) 5% Cremophor EL® plus 5% methanol in 10 mM sodium phosphate buffer (pH 7.0), b) 1% ODL-15 in 10 mM sodium phosphate buffer (pH 7.0), (b) 2% ODL-15 in 10 mM sodium phosphate buffer (pH 7.0) and the drug was administered intravenously and the dosing strength was 10 mg/kg. The AUC obtained from the IV administrations were, 7741, 8594 and 1477 for 1% of ODL-15, 2% of ODL-15 and Cremophor EL®, respectively.

Example 16

Preparation of Propofol Solution for Injection

A propofol solution suitable for intravenous delivery is prepared as follows. 5% (w/v) of OAPDL-PEG in Saline was added to a vessel equipped with a mixer propeller and 2% (w/v) of Propofol was added with constant mixing at ambient room temperature. Mixing was continued until the drug was visually dispersed. Equal volume of Saline was added to the vessel with adequate mixing. Mixing continued for another 30 minutes or until a homogenous solution was achieved. A sample formulation is described in Table 14.

TABLE 14

| Ingredient[1] | mg/mL |
|---|---|
| Propofol | 10.0 |
| PEG-carbohydrate-lipid | 25.0 |
| Sodium Chloride | 9.0 |
| Sodium Hydroxide | See below |
| Hydrochloric Acid | See below |
| Purified Water | qs 1 mL |

[1]preservative is not needed if sterile-filtered is used.

The PEG-lipid may be any of PEG-carbohydrate-lipid conjugates with a PEG chain consisting of between about 6 and 24 subunits. Sodium hydroxide is used to prepare a 10% w/w solution in purified water. The targeted pH is in a range of 4.5 to 7.5. The NaOH solution is used to adjust pH if necessary.

In Example 16, the final concentration of the PEG-carbohydrate-lipid is preferably between about 16 mg/mL and about 30 mg/mL. The weight ratio of the total PEG-lipid to Propofol is preferably between about 2.0 and 2.5. The average MW of PEG chains in the PEG-lipid is preferably less than about 1000. The aqueous solution of Propofol can be further sterilized by filtration and sealed in sterile containers.

In Example 16, less concentrated or less purified PEG-sugar-lipid will create a suspension instead of an aqueous solution. For instance, the final concentration of the PEG-carbohydrate-lipid is less than 1.5% (w/v), it will form a suspension. Similarly when the oligomer purity is 80% or less, regardless the concentration of the PEG-carbohydrate-lipid, an emulsified solution will be observed instead of a transparent solution.

Example 17

Pharmacokinetic Profile of Propofol Formulations

Groups of three male mice (B6D2F1), 4 weeks old and weights of 25 to 32 grams) were used for the studies. Pharmacokinetics (PK) were performed on heparinized mouse plasma samples obtained typically at after the bolus IV injection at 1, 3, 8, 12, 15, 20, 30, 45 and 60 minutes for Propofol. Samples were analyzed using a HPLC-MS method. To determine the level of the drug, the drug was first isolated from plasma with a sample pre-treatment. Acetonitrile were used to remove proteins in samples. An isocratic HPLC-MS/MS method was then used to separate the drugs from any potential interference. Drug levels were measured by MS detection with a multiple reaction monitoring (MRM) mode. PK data was analyzed using the WinNonlin program (ver. 5.3, Pharsight) compartmental models of analysis.

Figure 4:
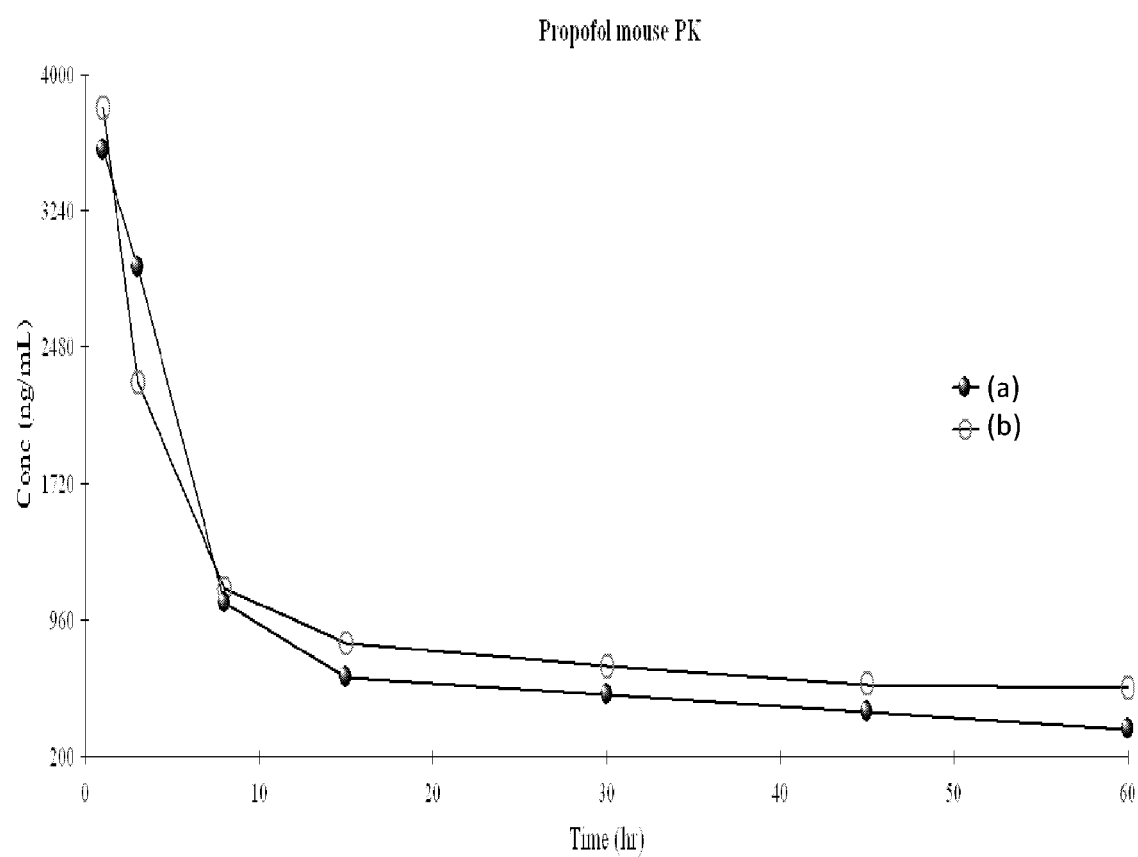
FIG. 4 shows pharmacokinetic profiles of Propofol formulations with (a) a commercial product of 1% Propofol (emulsified suspension) and (b) 1% of Propofol solution consisting of 2.3% of OAPDL-11 in saline after intravenous dosing.

FIG. 4 shows mouse PK profiles of propofol formulations with (a) a commercial product of 1% Propofol (emulsified suspension) and (b) 1% of Propofol in a formulation consisting of 2.3% of OAPDL-11 in saline solution. The drug was administered intravenously and the dosing strength was 20 mg/kg. From the 2-compartmental calculations, the AUC were 29.85 µg·min/mL with a half-life of 4.96 minutes for the commercial Propofol emulsified suspension (a) and 28.82 µg·min/mL with a half-life of 4.93 minutes for the Propofol solution (b) in OAPDL-11-saline, respectively.

In another aspect, the invention comprises a method of solubilizing a water-insoluble agent, i.e., a drug compound that, because of low solubility in water, typically requires formulation with a pharmaceutically acceptable carrier for effective delivery to an intended site of action. Such delivery may be intravenous, oral, topical, subdermal, sublingual, or any other mode of drug delivery. The invention also includes compositions for such delivery. Both the methods and the compositions related to delivery of water-insoluble agents employ the PEG-carbohydrate-lipid conjugates of the present invention and the methods and materials described above.

Unlike nature occurring lipids such as phospholipids, the conjugates of the present invention do not have a critical micellar concentration (CMC). Micelles only form when the concentration of surfactant is greater than the CMC, and the temperature of the system is greater than the critical micelle temperature. The present polymer-lipid conjugates form aggregates spontaneously at any given concentration.

The present invention discloses a novel polymer-lipid conjugate system having at least one of carbohydrate moiety that can be used as a safe and biocompatible vehicle for drug or molecule delivery. A therapeutic, diagnostic or cosmetic agent may be solubilized or encapsulated in those polymer-lipid conjugates to form a solution or micro-suspension.

Generally, the invention includes compositions and methods for synthesizing polymer-lipid-carbohydrate conjugates comprising a glycerol backbone or a linear multiamine or amino acid with a polymer (PEG) chain, a sugar (carbohydrate) and a lipid group bonded to the backbone. Spacer or linker groups including amino acids may be included between the backbone and the PEG chains, carbohydrates or and/or lipid groups. Furthermore, the terminal end of PEG chain may be a charged or polar moiety.

The compounds of the present invention are effective to formulate compositions of active agents whereby side effects and toxicities associated with therapeutic treatments are reduced.

In the present invention, the permeation enhancement properties of PEG-lipid conjugates can increase the in vivo targeted delivery of drugs, reduce toxicity and improve oral bioavailability of various drugs.

Solutions comprising conjugates of the present invention with solubilized active agents that can incorporate many active agents, including but not limited to propofol, cisplatin, docetaxel, voriconizole and gemcitabin.

Until now, the mechanism of pain following propofol injection has been unclear. Propofol belongs to the group of phenols that can directly irritate the skin, mucous membrane and venous intima and could immediately stimulate nociceptors and free nerve endings [Ambesh S P, Dubey P K, Sinha P K. "Ondansetron pretreatment to alleviate pain on propofol injection: a randomized, controlled, double-blinded study." *Anesth Analg.* 1999; 89: 197-9].

The concentration of aqueous free propofol is related to injection pain. By its indirect action on the endothelium, it was suggested that propofol activates the kallikrein-kinin system and releases bradykinin, thereby producing venous dilation and hyperpermeability, which increases the contact between aqueous phase of propofol and free nerve endings, results in delayed pain within half a minute [Briggs L P, Clarke R S, Dundee J W, Moore J, Bahar M, Wright P J. "Use of di-isopropyl phenol as main agent for short procedures." *Br J Anaesth.* 1981; 53: 1197-202; Scott R P, Saunders D A, Norman J. "Propofol: clinical strategies for preventing the pain of injection." *Anaesthesia.* 1988; 43: 492-4]. Recently several studies have suggested that propofol had no effect on the concentration of bradykinin in plasma, compared with saline control group [Lee E H, Lee S H, Park D Y, Ki K H, Lee E K, Lee D H, et al. "Physicochemical properties, pharmacokinetics, and pharmacodynamics of a reformulated microemulsion propofol in rats." *Anesthesiology.* 2008; 109: 436-47; Sim J Y, Lee S H, Park D Y, Jung J A, Ki K H, Lee D H, et al. "Pain on injection with microemulsion propofol." *Br J Clin Pharmacol.* 2009; 67: 316-25]. Therefore, the pain associated with propofol injection may be due to the sizes of propofol droplets; the free Propofol is in a range of 150 to 300 nm, which can slow down the migration or diffusion of the drug in the body and cause longer interactions between Propofol and free nerve endings.

It is well-known that PEG-Lipid and sugar have a pain-suppression effect [M. A. K. Mattila, M. Ruoppi, M. Korhonen, H. M. Larni, L. Valtonen and H. Heikkinen, "Prevention of Diazepam-Induced Thrombophlebitis with Cremophor as A Solvent," *Br. J. Aniesth.* 1979, 51: 891; Laura Johannes, "A Pinch of Sugar for Pain," *The Wall Street Journal.* Oct. 19, 2010].

Figure 5:
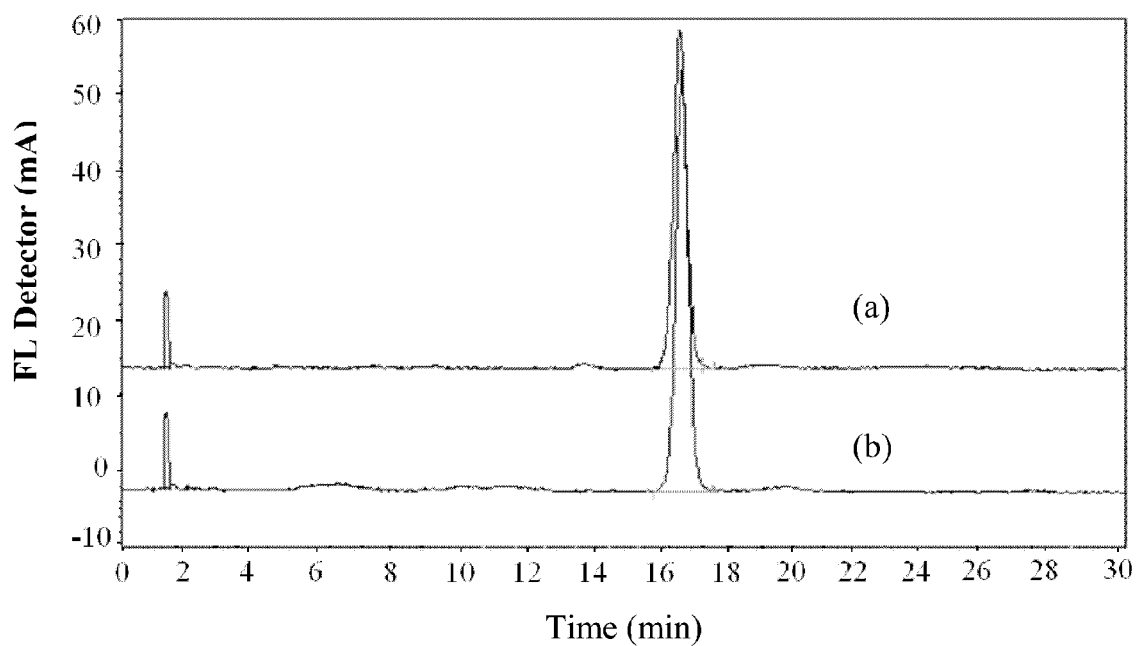
FIG. 5 shows that the HPLC-FL chromatograms of 1% Propofol solution (a) no filtration and (b) after filtered through a 0.2 μm Acrodisc® PF filter.

Propofol as the active agent was formulated with various polymer-lipid-carbohydrate conjugates described in the present invention. At a lower of the polymer-lipid-carbohydrate conjugate concentration, i.e., OAPDL-11 (<1.5%), the formulation is a microemulsion and at a higher OAPDL-11 concentration (≥2.2%), it is a true solution. FIG. 5 shows the HPLC-FL chromatogram of 1% Propofol solution with and without a filtration with 0.2 μm membrane filters.

A solution is defined as a homogenous mixture of substances with variable composition. In addition to their observed homogeneity, true solutions also have certain other characteristics. For example, components of a solution never separate spontaneously, even when a significant density difference exists between the components. Solutions also pass through the finest filters unchanged. FIG. 5 shows that the HPLC-FL chromatograms of 1%-Propofol formulated with 2.2% of OAPDL-11 in comparison with the same Propofol solution after filtered through a 0.2 μm Acrodisc® PF filter.

Further animal experiments found that the OAPDL-11 also showed an intravenous hydration effect which was better than free sugars for reducing renal toxicity of cisplatin [BLACHLEY, J D and HILL, J. "Renal and Electrolyte Disturbances Associated with Cisplatin." *Ann Intern Med.* 1981, 95: 628-632]. Groups of four each of mixed gender mice (B6D2F1), 2 to 3 weeks old and weights of 22 to 30 grams) were studied in duplicate. Each mouse was administrated cisplatin intravenously at a dose of 10 mg/kg (Table 15) and Intraperitoneally at a dose of 15 mg/kg (Table 16). The changes in body weights observed can be used as a direct evident in the renal toxicity effects.

TABLE 15

| | Group | Day 0 | Day 3 | Day 7 |
|---|---|---|---|---|
| (A) | 1 mg/mL of Cisplatin in Saline, pH = 3 (commercial dosage formula) | | | |
| | 1 | 24.8 | 23.7 | 24.9 |
| | 2 | 26 | 23.4 | 21.6 |
| | Weight change | 100% | 93% | 92% |
| (B) | same as (A) + 5%% mannitol | | | |
| | 1 | 24.3 | 23.6 | 22.0 |
| | 2 | 29.3 | 28.6 | 27.2 |
| | Weight change | 100% | 97% | 92% |
| (C) | 1 mg/mL of Cisplatin in 2% OAPDL-11 in saline, pH = 6 | | | |
| | 1 | 26.8 | 27.4 | 27.8 |
| | 2 | 27.1 | 27.3 | 27.9 |
| | Weight change | 100% | 101% | 103% |

TABLE 16

| | Group | Day 0 | Day 3 | Day 5 | Day 7 | Day 9 |
|---|---|---|---|---|---|---|
| (D) | 1 mg/mL of Cisplatin in Saline, pH = 3 (commercial dosage formula) | | | | | |
| | 1 | 27.5 | 24.3 | Died | | |
| | 2 | 24.9 | 20.1 | 19.4 | died | |
| | Weight change | 100% | 87% | 38% | | |
| (E) | 1 mg/mL of Cisplatin in 2% OAPDL-11 in saline, pH = 6 | | | | | |
| | 1 | 22.4 | 22.3 | 23.8 | 24.5 | 25.5 |
| | 2 | 23.2 | 23.1 | 24.1 | 24.8 | 25.9 |
| | 3 | 24.0 | 23.7 | 24.3 | 25.5 | 26.9 |
| | Weight change | 100% | 99% | 104% | 107% | 113% |

One feature or aspect of an embodiment is believed at the time of the filing of this patent application to possibly reside broadly in a chemical compound or a method of making a compound represented by the formula:

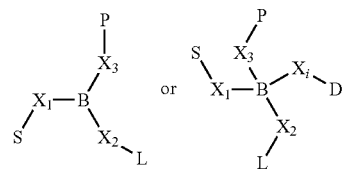

where X1, X2 and X3 are linking groups, Xi=X1 or X2 or X3; B is a central backbone, L is a lipid; S is a carbohydrate, P is a polymer and D is a Lipid or a carbohydrate or a polymer. The order of each conjugation position is not restricted on the backbone.

Another feature or aspect of an embodiment is demonstrated at the time of the filing of this patent application to possibly reside broadly in a chemical compound or a method of making a compound wherein a Polymer-carbohydrate-lipid conjugate with defined carriers is made by a method comprising the steps of:
(a) selecting a central backbone with at least three available sites for the conjugations between the three carriers and the central backbone;
(b) selecting a polymer as the first carrier;
(c) selecting a carbohydrate as the second carrier;
(d) selecting a lipid as the third carrier;
(e) selecting a terminal group on the polymer carrier;
(f) selecting a linker or linkers.

Yet another feature or aspect of an embodiment is demonstrated at the time of the filing of this patent application to possibly reside broadly in a chemical compound or a method of making a compound where the order of each conjugation step is not restricted and may further comprise the steps of:
(g) protecting the hydroxyl or amino group;
(h) bonding the first carrier to the central backbone;
(i) bonding the second carrier to the central backbone;
(j) removing the hydroxyl or amino protecting group; and
(k) bonding the third carrier to the central protecting group.

Still another feature or aspect of an embodiment is demonstrated at the time of the filing of this patent application to possibly reside broadly in a chemical compound or a method of making a compound wherein suitable molecules can be used as the backbone including glycerol or glycerol-like analogues or polyamines or amino acids or triols or diols with a carboxy group or amine or diamines with a hydroxyl or carboxy group and extensible amines or alcohols.

A further feature or aspect of an embodiment is demonstrated at the time of the filing of this patent application to possibly reside broadly in a chemical compound or a method of making a compound wherein a variety of compounds can be used as for the backbone with at least three or four available binding positions or molecules can be chemically extended to three binding sites from two available binding positions including and not limited to ethylenediamine or diaminopropane or ethanolamine or aminopropanol. In addition, a central backbone also comprises a compound with three said available binding positions or sites selected from the group consisting of glycerol or glycerol-like analogues, triamines, triols, triacids, amino acids, said compound being chemically extended and modified to provide said fourth available binding position or site. More preferable the space between the two closest binding positions on the backbone is between 2 to 8 subunits such as single carbon or CH2. Most preferable space between the two closest binding positions on the backbone is between 2 and 4 subunits.

Another feature or aspect of an embodiment is demonstrated at the time of the filing of this patent application to possibly reside broadly in a chemical compound or a method of making a compound wherein the polymer is a PEG having subunits between 5 and 45. The PEG chain may consist of between about 3 and 45 subunits. More preferably the PEG chain consists of between about 5 and 24 subunits. Still more preferably the PEG chain consists of between about 8 and 16 subunits.

Yet another feature or aspect of an embodiment is demonstrated at the time of the filing of this patent application to possibly reside broadly in a chemical compound or a method of making a compound where the polymer is a branched PEG having 2 or more subchains each chain having a PEG subunits between 5 and 45.

Still another feature or aspect of an embodiment is demonstrated at the time of the filing of this patent application to possibly reside broadly a chemical compound or a method of making a compound wherein the PEG-carbohydrate-lipid is a compound represented by the formulas of the General Structure 1 trough 16.

A further feature or aspect of an embodiment is demonstrated at the time of the filing of this patent application to possibly reside broadly in a chemical compound or a method of making a compound wherein the lipid group is selected from diacylglycerols and the alkyl groups in Table 3 and Table 4 or steroid acid in Table 5

Another feature or aspect of an embodiment is demonstrated at the time of the filing of this patent application to possibly reside broadly in a chemical compound or a method of making a compound wherein the carbohydrate is a carbohydrate including monosaccharides or disaccharides or oligosaccharides selected from Table 6.

Yet another feature or aspect of an embodiment is demonstrated at the time of the filing of this patent application to possibly reside broadly in a chemical compound or a method of making a compound wherein the linker is selected from the group consisting of —S—, —O—, —N—, —OCOO—, and the linkers in Tables 1 and 2.

Another feature or aspect of an embodiment is demonstrated at the time of the filing of this patent application to possibly reside broadly in a chemical compound or a method of making a compound wherein preferable amino acid linkers are Proline, Glycine, Alanine, Lysine, Cysteine, Valine, Isoleucine, Leucine, Methionine, Phenylalanine, Histidine, Tryptophan, Tyrosine, Selenocysteine, and Arginine.

Yet another feature or aspect of an embodiment is demonstrated at the time of the filing of this patent application to possibly reside broadly in a chemical compound or a method of making a compound wherein the central backbone is those glycerol or glyceride or triols or aminodiols and analogues selected from the group consisting of 3-amino-1,2-propanediol, 3-bromo-1,2-propanediol, 3-chloro-1,2-propanediol, 3-fluoro-1,2-propanediol, DL-glyceric acid, diaminopropionic acid, tartaric acid, glucoheptonic acid and, 2,4-butanetriol, 2,2-Bis(hydroxymethyl)butyric acid, 1,3-Diamino-2-propanol and 2-(3-Aminopropylamino)-ethanol. 3-amino-1,2-propanediol, 3-bromo-1,2-propanediol, 3-chloro-1,2-propanediol, 3-fluoro-1,2-propanediol, DL-glyceric acid, diaminopropionic acid, tartaric acid, glucoheptonic acid and, 2,4-butanetriol, 2,2-bis(hydroxymethyl)butyric acid, 1,3-Diamino-2-propanol and 2-(3-Aminopropylamino)ethanol. 3-((3-aminopropyl)-amino)propanol.

Still another feature or aspect of an embodiment is demonstrated at the time of the filing of this patent application to possibly reside broadly in a chemical compound or a method of making a compound wherein the central backbone is a linear amine including diethylenetriamine, spermidine, triethylenetetramine, spermine, norspermidine, bis(3-aminopropyl)-1,3-propanediamine, bis(hexamethylene)triamine, spermidine, tris(hydroxymethyl)aminomethane, diaminobenzidine, threitol, meso-erythritol, arginine, oxylyldiaminopropionic acid.

A further feature or aspect of an embodiment is demonstrated at the time of the filing of this patent application to possibly reside broadly in a chemical compound or a method of making a compound wherein the central backbone is selected from a group consisting of a amino acid with two carboxyl groups or two hydroxyl or two amino groups including aspartic acid, glutamic acid, asparagine, glutamine, ornithine, serine and threonine, more preferable are aspartic acid, glutamic acid, ornithine, serine and threonine.

Another feature or aspect of an embodiment is demonstrated at the time of the filing of this patent application to possibly reside broadly in a chemical compound or a method of making a compound wherein the PEG chain is perfectible monodisperse for intravenous administration of pharmaceutical agents and the monodisperse PEG chain may contain a few numbers of oligomers. The preferable number of oligomers is 1 to 5, more preferable is 1 to 3. Most preferable is 1 to 2.

Yet another feature or aspect of an embodiment is demonstrated is believed at the time of the filing of this patent application to possibly reside broadly in a chemical compound or a method of making a compound wherein the PEG chains are replaced by polymers selected from the group consisting of polymethylene glycol, polypropylene glycol, and copolymers comprised of a at least two of the monomers selected from the group consisting of methylene glycol, propylene glycol and ethylene glycol.

Still another feature or aspect of an embodiment is demonstrated at the time of the filing of this patent application to possibly reside broadly in a chemical compound or a method of making a compound wherein the terminal (R) group is preferably easily polarized or negatively or positively charged head-groups such as alkoxy moieties, amines, amino acids, and oligosaccharides.

A further feature or aspect of an embodiment is demonstrated at the time of the filing of this patent application to possibly reside broadly in a chemical compound or a method of making a compound wherein the composition for delivery of an active agent, comprising: a chemical compound is represented by the formula:

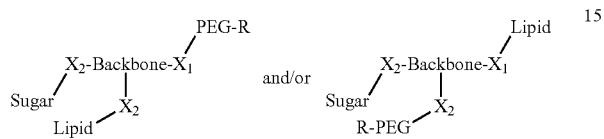

where X1, X2 and X3 are linking groups; and the active agent is a poorly water soluble compound of Biopharmaceutics classification II or IV including but not limited to propofol, docetaxel, paclitaxel, voriconazole and posaconazole.

Another feature or aspect of an embodiment is demonstrated at the time of the filing of this patent application to possibly reside broadly in a method of delivering a compound, the method comprising preparing a polymer-carbohydrate-lipid conjugate(s) based formulation of the compound, where the formulation comprises a PEG-carbohydrate-lipid conjugate having the three carrier groups.

Yet another feature or aspect of an embodiment is demonstrated at the time of the filing of this patent application to possibly reside broadly in a method of preparing a pharmaceutical formulation of a therapeutic agent, the method comprising:

(a) determining a therapeutic target;

(b) determining a mode of administration;

(c) determining the physiological conditions the PEG-carbohydrate-lipid based formulation will encounter in reaching the therapeutic target using the mode of administration; and selecting a PEG-carbohydrate lipid having one or more linkers between the three carriers including a PEG chain, a carbohydrate and a fatty acid or steroid acid and the central backbone or amino acid or linear multiamine backbond, where such selecting is informed by the physiological conditions; and combining the PEG-carbohydrate-lipid conjugates and the therapeutic agent in a pharmaceutical formulation.

Another feature or aspect of an embodiment is demonstrated at the time of the filing of this patent application to possibly reside broadly in a chemical compound or a method of making a compound wherein the therapeutic agent is Propofol; and where the weight ratio of the PEG-carbohydrate-lipid to the drug compound is between about 1 and 3.

While preferred embodiments of the present invention have been described, those skilled in the art will recognize that other and further changes and modifications can be made without departing from the spirit of the invention, and all such changes and modifications should be understood to fall within the scope of the invention.

While preferred embodiments of the present invention have been described, those skilled in the art will recognize that other and further changes and modifications can be made without departing from the spirit of the invention, and all such changes and modifications should be understood to fall within the scope of the invention.

The invention claimed is:

1. A PEG-Carbohydrate-Lipid Conjugate selected from the group consisting of:

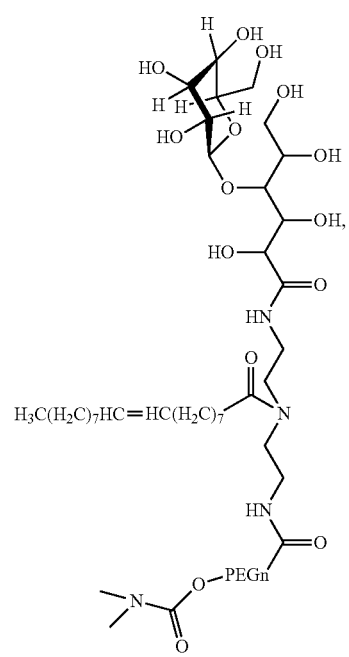

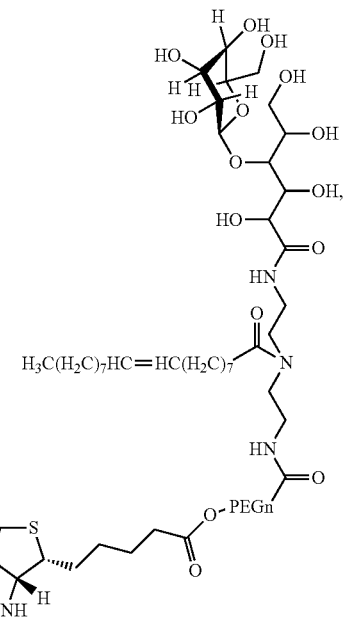

65
-continued
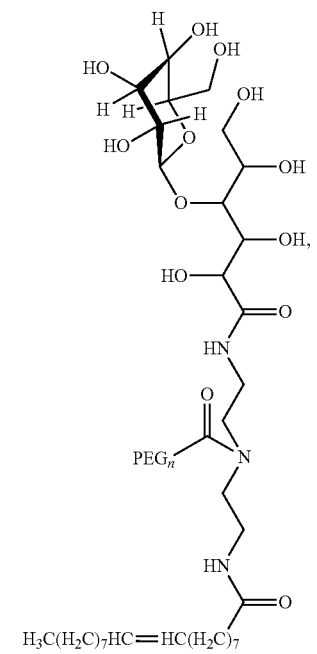
66
-continued
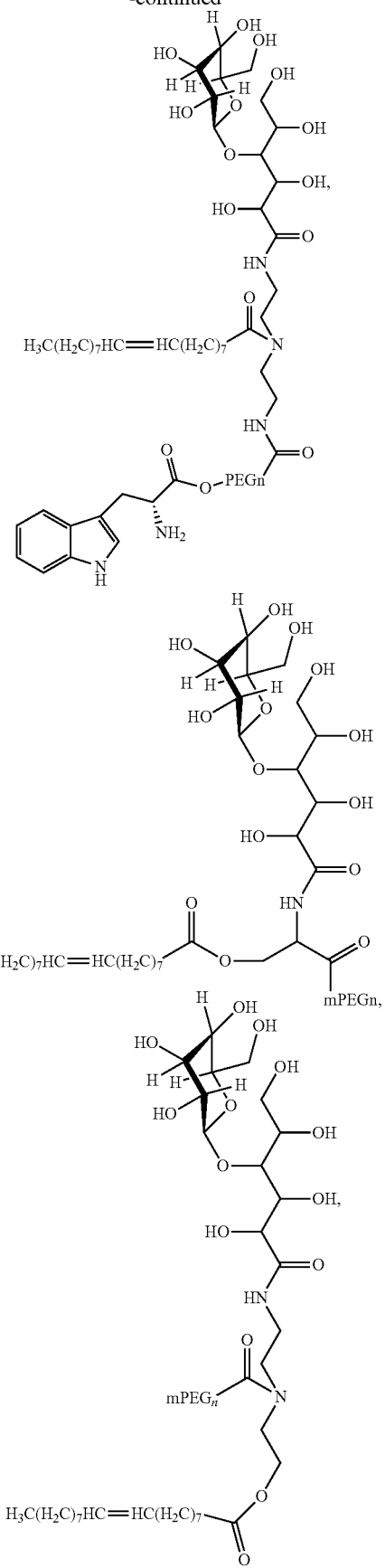

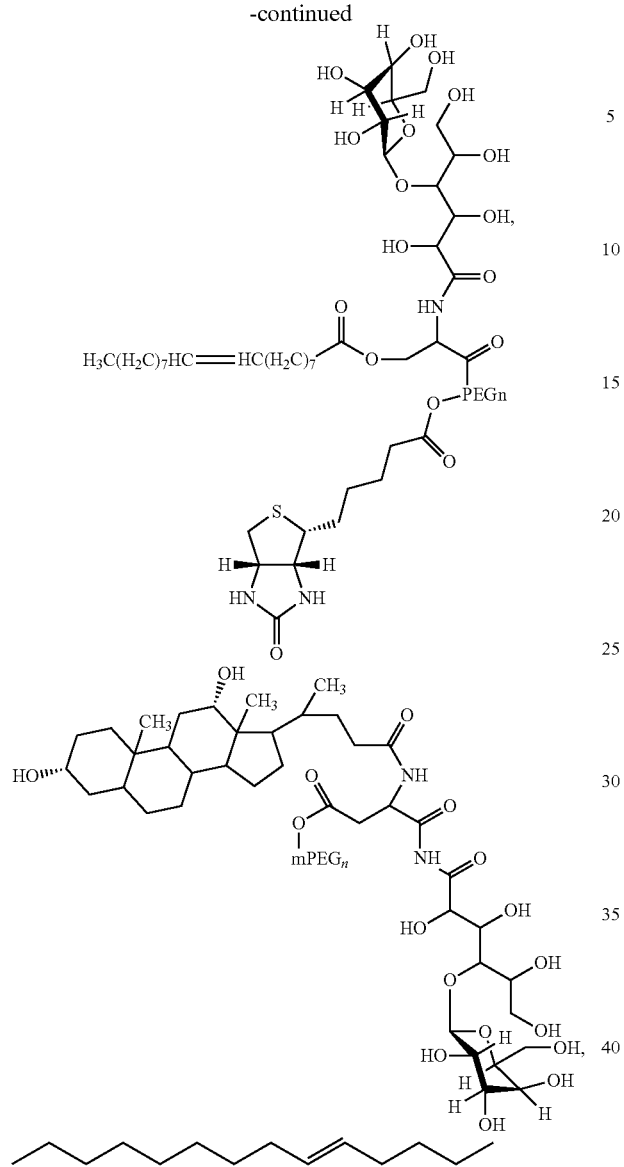
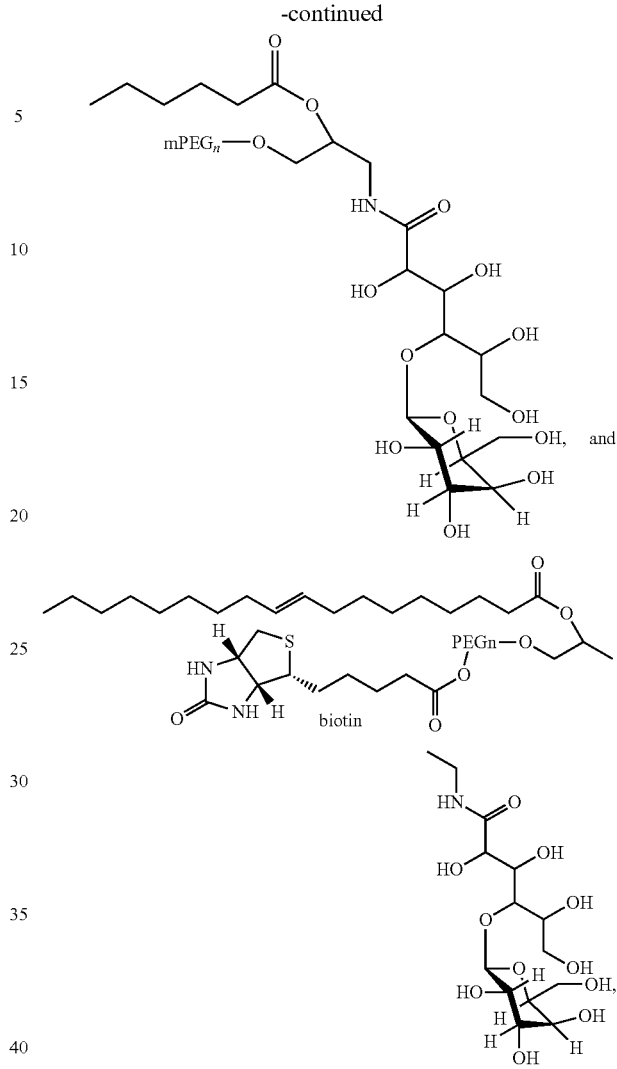
wherein PEG is polyethylene glycol and n = 6 to 24.
* * * * *